(12) United States Patent
Pathy et al.

(10) Patent No.: US 11,622,831 B2
(45) Date of Patent: Apr. 11, 2023

(54) LIGHTING DEVICE FOR HANDHELD SURGICAL INSTRUMENT WITH SMOKE EVACUATION SYSTEM

(71) Applicant: Pathy Medical, LLC, Shelton, CT (US)

(72) Inventors: Vinod V. Pathy, Shelton, CT (US); Gennady Kleyman, Brooklyn, NY (US)

(73) Assignee: Pathy Medical, LLC, Shelton, CT (US)

( * ) Notice: Subject to any disclaimer, the term of this patent is extended or adjusted under 35 U.S.C. 154(b) by 377 days.

(21) Appl. No.: 16/923,182

(22) Filed: Jul. 8, 2020

(65) Prior Publication Data

US 2021/0022826 A1    Jan. 28, 2021

Related U.S. Application Data

(63) Continuation of application No. 16/519,744, filed on Jul. 23, 2019, now Pat. No. 10,716,642.

(51) Int. Cl.
| | |
|---|---|
| *A61B 90/35* | (2016.01) |
| *A61B 18/14* | (2006.01) |
| *F21V 33/00* | (2006.01) |
| *F21V 23/04* | (2006.01) |
| *F21V 21/088* | (2006.01) |

(Continued)

(52) U.S. Cl.
CPC .............. *A61B 90/35* (2016.02); *A61B 18/14* (2013.01); *F21V 21/0885* (2013.01); *F21V 23/0414* (2013.01); *F21V 33/0068* (2013.01); *F21V 33/0096* (2013.01); *A61B 2018/00595* (2013.01); *A61B 2018/00601* (2013.01); *A61B 2218/008* (2013.01); *F21Y 2115/10* (2016.08)

(58) Field of Classification Search
CPC combination set(s) only.
See application file for complete search history.

(56) References Cited

U.S. PATENT DOCUMENTS

| 5,674,219 A | 10/1997 | Monson et al. |
| 8,876,709 B2 | 11/2014 | Vayser et al. |

(Continued)

FOREIGN PATENT DOCUMENTS

| JP | 2014506152 | 3/2014 |
| WO | 2017031245 A1 | 2/2017 |

OTHER PUBLICATIONS

PlumePen Ultra—Surgical Smoke Evacuation Pencil—Buffalo Filter (2018).

(Continued)

*Primary Examiner* — Sameh R Boles
(74) *Attorney, Agent, or Firm* — Locke Lord LLP; Scott D. Wofsy; Michael J. Pollack

(57) ABSTRACT

A lighting device for attachment to a handheld electrosurgical instrument is disclosed, which includes an elongated housing having opposed proximal and distal end portions and defining an interior chamber containing a battery powered light assembly for illuminating a surgical site, the housing having at least one smoke evacuation passage that extends from an inlet located adjacent to or near the distal end portion of the housing to an outlet located adjacent to or near the proximal end portion of the housing for removing smoke generated at the surgical site.

6 Claims, 32 Drawing Sheets

(51) Int. Cl.
  *F21Y 115/10*    (2016.01)
  *A61B 18/00*    (2006.01)

(56)        References Cited

U.S. PATENT DOCUMENTS

|     |     |     |     |
| --- | --- | --- | --- |
| 9,851,060 | B2 | 12/2017 | Pathy |
| 10,213,249 | B2 | 2/2019 | Cosmescu |
| 2006/0211918 | A1 | 9/2006 | Lieponis |
| 2014/0293590 | A1 | 10/2014 | Pathy |
| 2015/0359581 | A1 | 12/2015 | Albertal |
| 2016/0278874 | A1 | 9/2016 | Fleenor |
| 2018/0110404 | A1 | 4/2018 | Devaiah et al. |
| 2018/0110582 | A1 | 4/2018 | Warnock |
| 2018/0153635 | A1 | 6/2018 | Preissman |
| 2018/0318034 | A1 * | 11/2018 | Julian Ibañez ...... A61B 90/361 |
| 2021/0022796 | A1 | 1/2021 | Kleyman et al. |

OTHER PUBLICATIONS

PCT International Search Report and Written Opinion dated Oct. 14, 2021, issued during the prosecution of PCT International Patent Publication No. PCT/US2021/038614.
International Preliminary Report on Patentability issued in PCT/US2020/039762, dated Jan. 25, 2022.

* cited by examiner

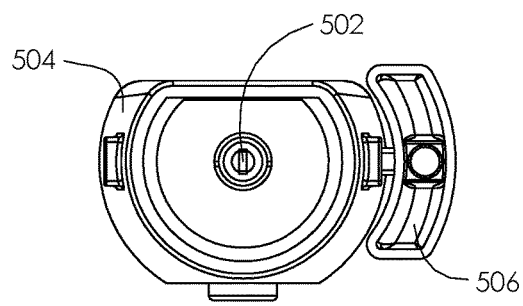
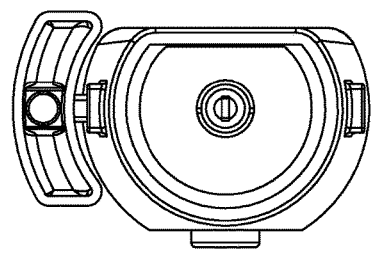
FIG. 28  FIG. 29
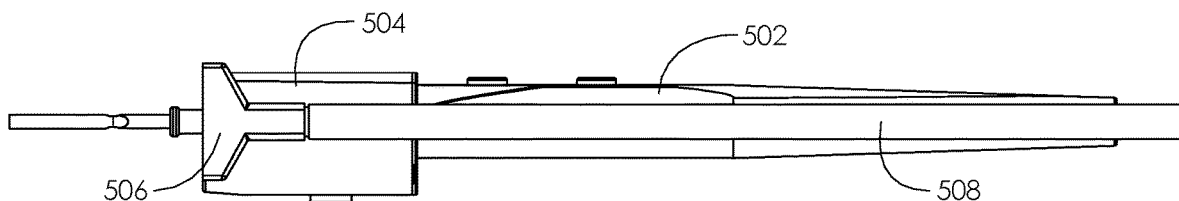
FIG. 30
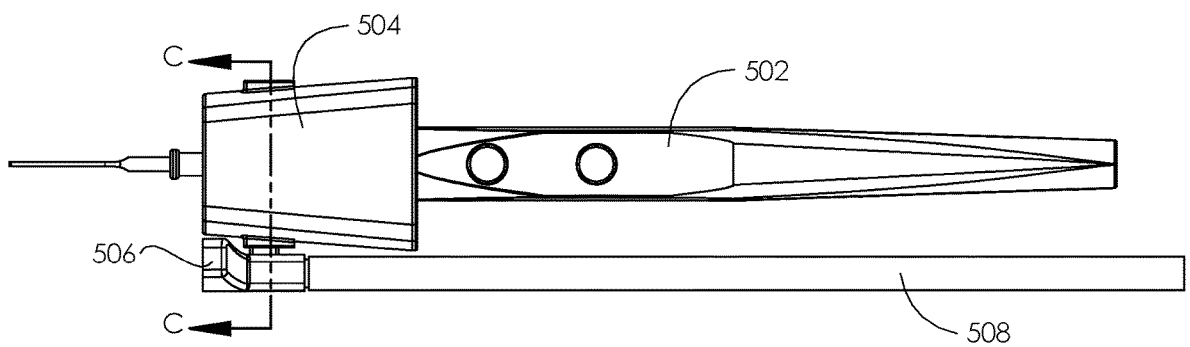
FIG. 31
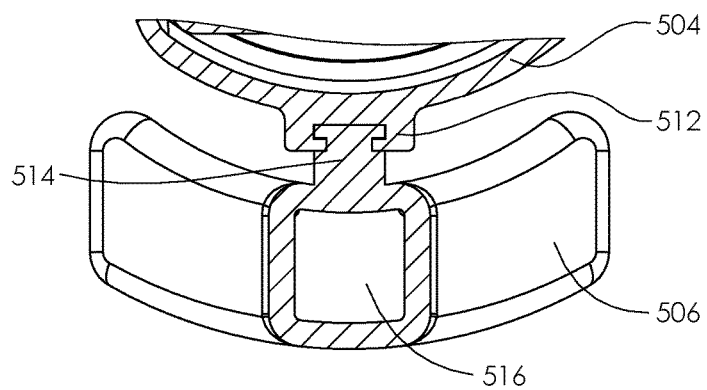
FIG. 32

LIGHTING DEVICE FOR HANDHELD SURGICAL INSTRUMENT WITH SMOKE EVACUATION SYSTEM

CROSS-REFERENCE TO RELATED APPLICATIONS

This Application is a Continuation of U.S. patent application Ser. No. 16/519,744 filed on Jul. 23, 2019, which is incorporated herein by reference in its entirety.

BACKGROUND OF THE INVENTION

1. Field of the Invention

The subject invention is directed to surgical instrumentation, and more particularly, to a battery powered lighting device used with a handheld electrosurgical instrument, which includes a smoke evacuation system.

2. Description of Related Art

In medical practice, lighting devices are used to direct light at a specific area being operated on or examined. For example, lighting devices can be used in conjunction with a handheld electrosurgical device, such as a BOVIE® pencil, which is typically used to incise tissue during a surgical procedure.

Some instruments known in the art include an integral light source, but these devices are generally expensive and relatively bulky. Cordless and corded lighting devices for surgical tools are also known in the art, but these can also add bulk, preventing a user from manipulating the tool with precision or in confined spaces.

Additionally, many lighting devices, especially corded devices and overhead lights, require constant repositioning, are assistant-dependent to hold or re-position, and can be disruptive to a surgical field. Furthermore, corded lighting devices, as well as light sources that are integrated into a tool can become hot, burning the user and/or patient, and possibly even causing a fire.

Headlights can be used as an alternative to a lighting device during a surgical procedure. However, similar to lighting devices, headlights are bulky, commonly require cables to connect to a power source, require constant readjustment, and can pose a potential safety hazard. Moreover, being worn on the head of the surgeon, they are at a distance from the surgical field, decreasing their effectiveness, and they can cause fatigue and strain if worn for an extended period of time.

It is known that when handheld lighting devices, overhead lights and/or headlamps are employed during a surgical procedure, the hands/tools of the surgeon can block the light and cast a shadow on the surgical site, which is undesirable. Those shadows require the user to reposition the lighting sources regularly, and can even require the surgeon to move their head to try to angle the headlamp towards the surgical site differently.

A particularly useful battery powered lighting device designed for attachment to a handheld electrosurgical device, and in particular, for use with a BOVIE® pencil, is disclosed in commonly assigned U.S. Pat. No. 9,851,060, the disclosure of which is herein incorporated by reference in its entirety. This device overcomes the deficiencies of the prior art lighting devices described above.

The use of a handheld electrosurgical device, such as a BOVIE® pen to incise tissue, typically creates surgical smoke when energy is imparted to tissue cells during surgery. The heat from the energy vaporizes the intracellular fluid, which increases the pressure inside the cell and eventually causes the cell membrane to burst. When this happens, a plume of smoke containing mostly water vapor is released into the operating room. At the same time, the heat chars the protein and other organic matter within the cell, releasing contaminants, such as carbonized cell fragments and gaseous hydrocarbons.

These small particles and gases are potentially hazardous if inhaled. If they are not evacuated from the surgical site nearest to the location where the surgical smoke is created, they can become airborne and inhaled. This has led to the development and use of smoke evacuation systems during surgical procedures. A smoke evacuator is basically a vacuum pump with one or more filters designed to remove surgical smoke and aerosol from an operative site and filter out contaminants. In addition, they may return filtered air to the operating room.

Given the increasing need and desire for surgical evacuation systems in operating rooms, the inventors have determined that it would be advantageous to incorporate such a system directly into a battery powered lighting device used with a handheld electrosurgical instrument. The subject disclosure presents several new and useful embodiments of a battery powered lighting device for use with an electrosurgical instrument, such as a BOVIE® pencil, which incorporates a smoke evacuation system.

SUMMARY OF THE DISCLOSURE

The subject invention is directed to new and useful lighting devices for installation on a handheld surgical instrument, and preferably, for releasable attachment to a handheld electrosurgical instrument. More particularly, the subject invention is directed to a lighting device for attachment to a handheld electrosurgical instrument that includes an elongated housing having opposed proximal and distal end portions and defining an interior chamber containing a battery powered light assembly for illuminating a surgical site, wherein the housing has at least one smoke evacuation passage associated therewith that extends from an inlet located adjacent, near or proximate to the distal end portion of the housing to an outlet located adjacent, near or proximate to the proximal end portion of the housing for removing smoke generated at the surgical site.

In one embodiment of the lighting device, the smoke evacuation passage is located within the housing of the lighting device, separated from the interior chamber by an interior wall of the housing. In another embodiment of the lighting device, the smoke evacuation passage is located outside of the housing of the lighting device, separated from the interior chamber by an exterior wall of the housing.

A connective fitting is associated with the outlet of the smoke evacuation passage for connecting the smoke evacuation passage with a smoke evacuation tube that communicates with a source of suction. Preferably, a filter element is located within at least one of the smoke evacuation passage or located in the smoke evacuation tube. It is envisioned that the smoke evacuation passage could have any cross-sectional configuration, including, for example, a rectangular cross-sectional configuration, a square cross-sectional configuration, an oval cross-sectional configuration or a circular cross-sectional configuration.

In yet another embodiment of the lighting device, the associated smoke evacuation passage extends through a nozzle assembly that is detachably connected to an exterior side wall of the housing of the lighting device. In such an embodiment, the nozzle assembly may be detachably connected to an exterior side wall of the housing by way of a snapping connection mechanism, including an engagement flange on the exterior wall of the housing and a pair of deflectable engagement tangs on the nozzle assembly, or vice versa. Alternatively, the associated nozzle assembly may be detachably connected to an exterior side wall of the housing by way of a sliding tongue and groove connection mechanism, including a groove portion on the exterior wall of the housing and a tongue portion on the nozzle assembly, or vice versa. In yet another embodiment, the nozzle assembly may be detachably connected to an exterior side wall of the housing by way of an adhesive strip.

Preferably, the associated nozzle assembly includes an inlet nozzle, a smoke evacuation tube extending proximally from the inlet nozzle and a barbed connective fitting at a proximal end of the smoke evacuation tube. The inlet nozzle includes at least one inlet orifice adapted and configured to maximize smoke evacuation coverage and performance, because the inlet nozzle can be positioned close to cautery site where the smoke is created. In this regard, it is also envisioned that the inlet nozzle could be configured to telescope or otherwise extend distally so that it may be positioned is in close proximity to source of smoke creation.

A filter element can be disclosed in at least one of the inlet nozzle, barbed connective fitting, or the smoke evacuation tube. A coupling is operatively associated with the smoke evacuation tube for securing the tube to a surgical instrument.

Preferably, the battery powered lighting assembly includes a printed circuit board that includes at least one LED lighting component, at least one battery cell, and a switching mechanism. An actuation button is associated with the housing for actuating the switching mechanism. In an embodiment of the invention, at least one rotatable fans is located within the smoke evacuation passage, and it is operatively connected to the printed circuit board of the battery powered light assembly. The fan may be configured to direct air flow from the smoke evacuation passage or to draw air flow into the smoke evacuation passage.

In an embodiment of the subject invention, the housing of the lighting device includes a clamping mechanism for selectively attaching the lighting device to the surgical instrument. The clamping mechanism include a generally U-shaped clamp body having a pair of opposed parallel clamping arms, and wherein an adjustable holding screw is associated with one clamping arm and an interior surface of the other clamping arm has a compliant material plate thereon. The clamping mechanism is pivotably connected to the housing about a pivot axis that extends perpendicular to a longitudinal axis of the elongated housing.

In another embodiment of the subject invention, the interior chamber of the housing has conical bore for receiving a distal end portion of the surgical instrument. In this embodiment, the battery powered lighting assembly is adapted and configured to activate or otherwise turn on when the distal end portion of the surgical instrument is received within the conical bore. Conversely, the battery powered lighting assembly is adapted and configured to deactivate or otherwise turn off when the distal end portion of the surgical instrument is removed from the conical bore.

The subject invention is also directed to a kit for performing a surgical procedure that includes a packaging enclosure, a battery powered lighting device contained within the packaging enclosure configured for attachment to a handheld surgical instrument, and a smoke evacuation nozzle assembly contained within the packaging enclosure configured for attachment to the lighting device. The kit may further include a handheld surgical instrument within the packaging enclosure for performing a surgical procedure.

Preferably, the smoke evacuation nozzle assembly includes an inlet nozzle, a smoke evacuation tube extending proximally from the inlet nozzle and a barbed connective fitting at a proximal end of the smoke evacuation tube, and a clamping mechanism is associated with the tube for selectively attaching the tube to a surgical instrument.

The subject invention is also directed to a method for performing a surgical procedure including the steps of attaching a lighting device to a surgical instrument wherein the lighting device has a smoke evacuation passage associated therewith, either integrally or connectively, and connecting an outlet of the smoke evacuation passage to a source of suction, such as, for example, a smoke evacuator or suction device. The method may further include the steps of using the surgical instrument to perform electrocautery, and activating the source of suction to perform smoke evacuation through an inlet of the smoke evacuation passage.

Preferably, the step of attaching the lighting device to the surgical instrument includes automatically activating a light source of the lighting device, and the method further includes the step of removing the lighting device from the surgical instrument and thereby automatically deactivating the light source. Preferably, the step of connecting an outlet of the smoke evacuation passage to a source of suction includes attaching a smoke evacuation tube to a first side of the lighting device, and the method further includes the steps of detaching the smoke evacuation tube from the first side of the lighting device and reattaching the smoke evacuation tube to a second side of the lighting device.

These and other features of the lighting devices of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the lighting device of the subject invention without undue experimentation, preferred embodiments thereof will be described in detail herein below with reference to the figures wherein:

FIG. 28 is a front elevational view of the assembly shown in FIG. 27 illustrating a left side attachment;

FIG. 29 is a front elevational view of the assembly shown in FIG. 27 illustrating a right side attachment;

FIG. 30 is a right side elevational view of the assembly shown in FIG. 27;

FIG. 31 is a top plan view of the assembly shown in FIG. 27;

FIG. 32 is a partial section view taken along line C-C of FIG. 31;

DETAILED DESCRIPTION OF THE PREFERRED EMBODIMENTS

Figure 1:
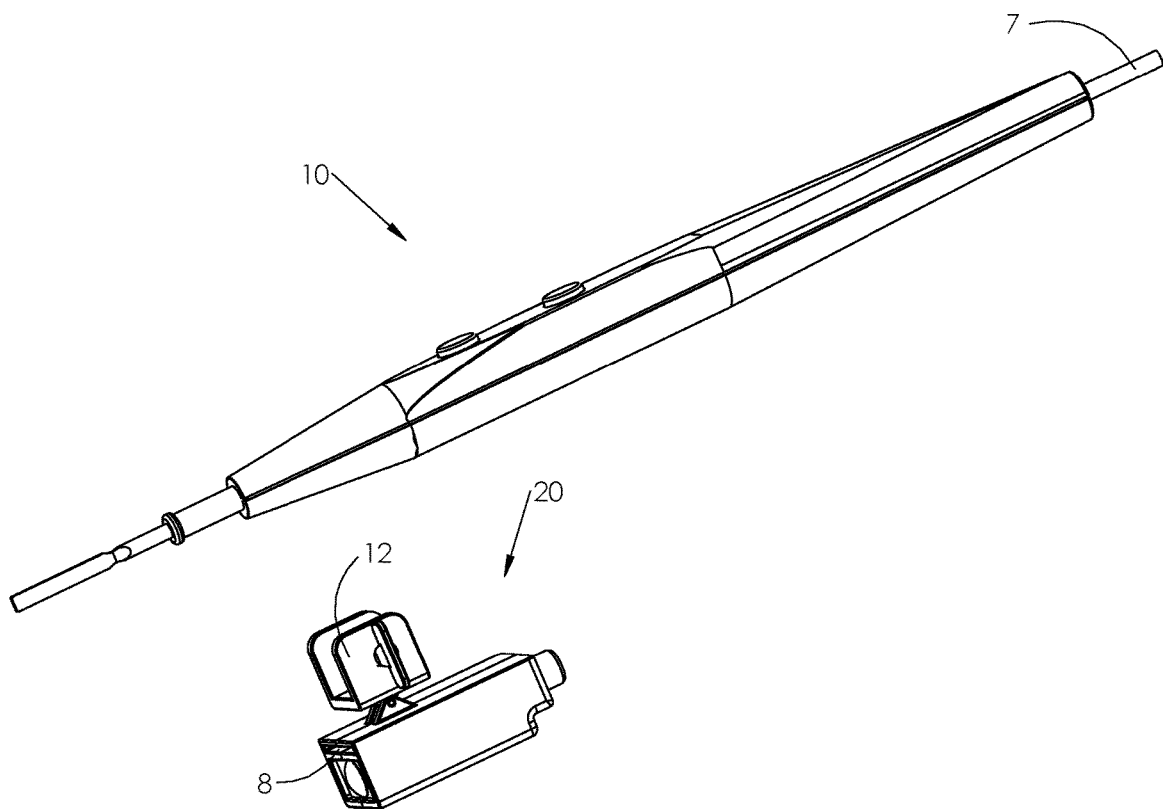
FIG. 1 is a perspective view of a lighting device having an internal smoke evacuation passage separated from a surgical instrument to which it may be attached.
Figure 2:
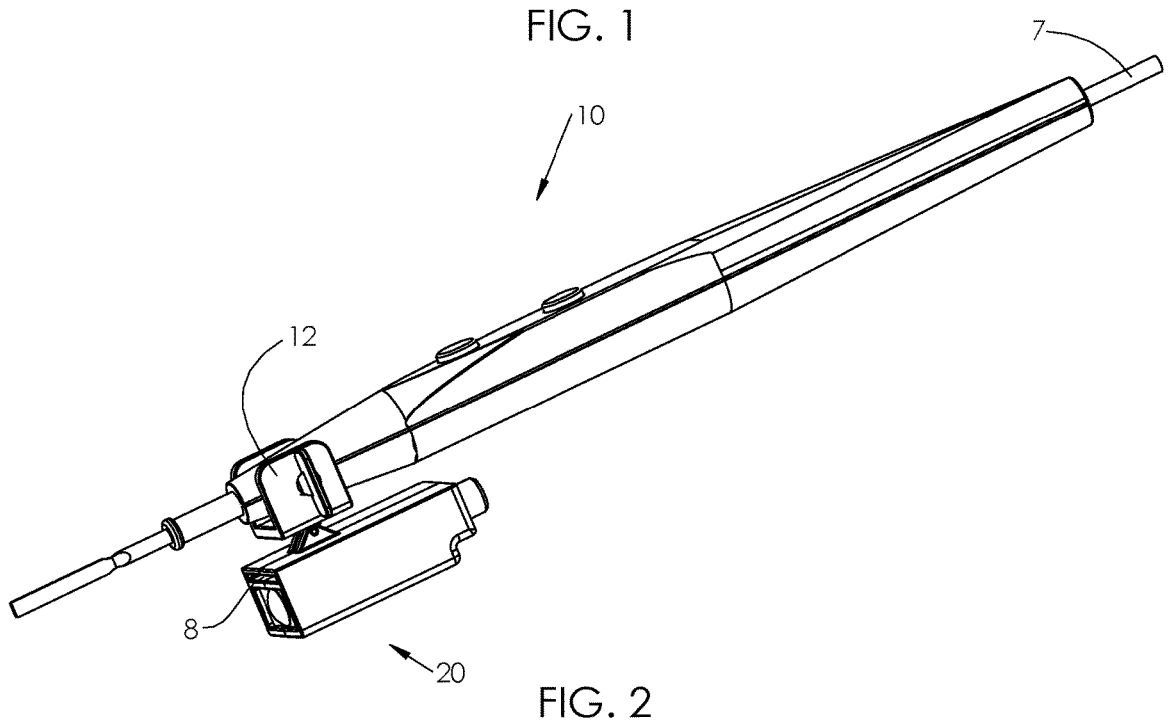
FIG. 2 is a perspective view of the lighting device with internal smoke evacuation passage attached to the surgical instrument shown in FIG. 1.
Figure 3:
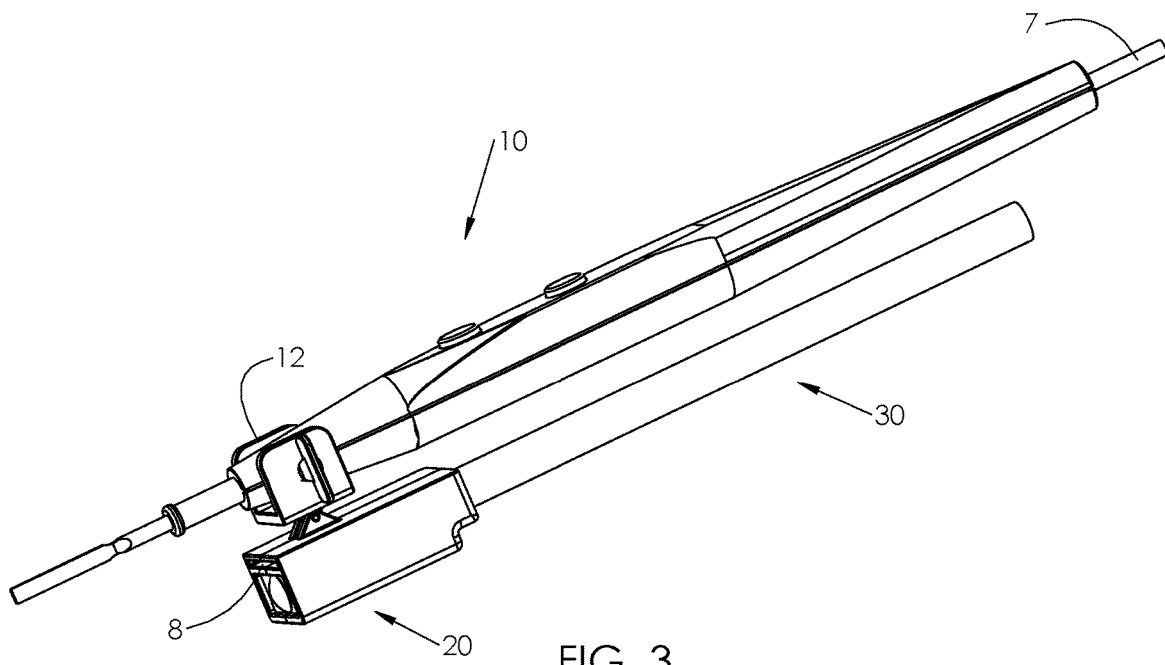
FIG. 3 is a perspective view of the lighting device with internal smoke evacuation passage attached to a surgical instrument, with smoke evacuation tubing connected thereto.

Referring now to the drawings wherein like reference numerals identify similar structural elements of the various embodiments of the subject invention, there is illustrated in FIG. 1 a lighting device 20 having an internal smoke evacuation passage 8. The lighting device 20 is adapted and configured to be attached to a surgical instrument 10, preferably on the distal end portion thereof, as shown in FIG. 2. As shown in FIG. 3, an elongated smoke evacuation tube 30 connects the proximal end of the internal smoke evacuation passage 8 of lighting device 20 to a source of suction such as smoke evacuator or pump (not shown).

Figure 12:
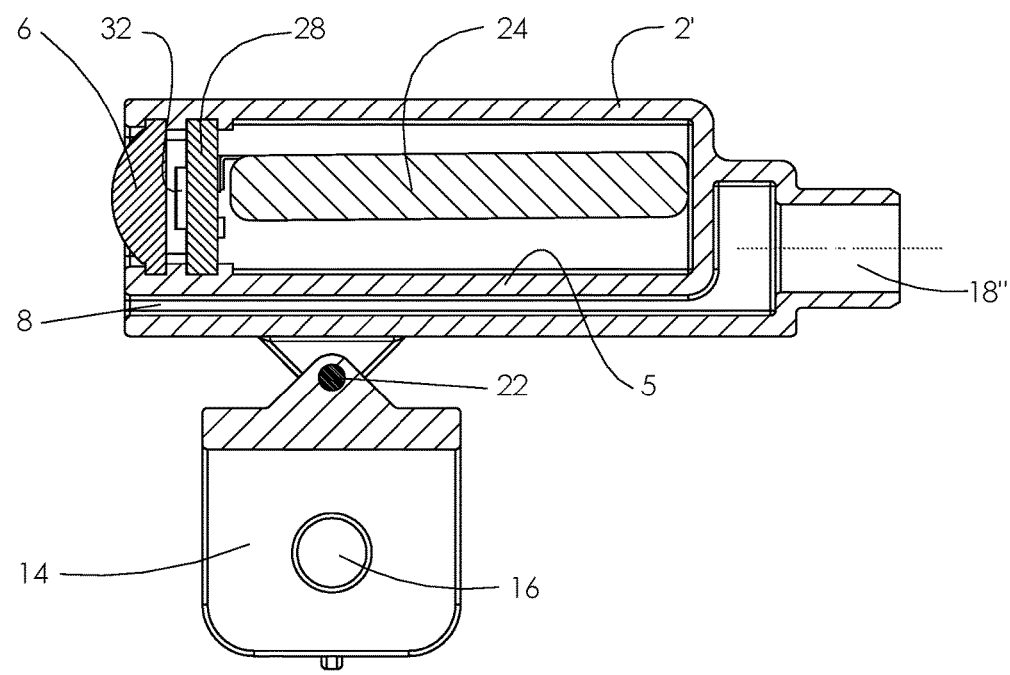
FIG. 12 is a cross-sectional view of the lighting device with internal smoke evacuation passage taken along line A-A of FIG. 7.

Referring now to FIGS. 4 through 12, the lighting device 20 has a generally rectangular housing with opposed proximal and distal ends defined by left and right housing components 2 and 2'. As best seen in FIG. 12, the housing of lighting device 20 defines an interior chamber that contains a battery powered light assembly for illuminating a surgical site. The light assembly includes a printed circuit board 28 with at least one or two integrated or embedded LED light components 32, a mechanical switching mechanism 26, and a battery cell 24. A concave lens 6 is located at the distal end of the housing for directing the light sources 32.

A push button actuator 4 is associated with the housing section 2 for manually actuating the switching mechanism 26 that controls the battery powered light assembly. The housing defined by left and right housing components 2 and 2' includes the internal smoke evacuation passage 8, which is defined by left and right passage portions 8 and 8' best seen in FIG. 11. Smoke evacuation passage 8 is separated from the interior chamber of the housing by an interior wall 5. The smoke evacuation passage 8 extends from an inlet located adjacent the distal end portion of the housing to an outlet or connective fitting 18, 18' located adjacent the proximal end portion of the housing. Connective fitting 18 enables the elongated smoke evacuation tube 30 to connect the smoke evacuation passage 8 with a source of suction, such as a smoke evacuator (not shown).

Referring to FIGS. 6 through 10, the lighting device 20 includes a clamping mechanism 12 for selectively attaching the lighting device to the surgical instrument, as seen in FIG. 2. The clamping mechanism 12 includes a generally U-shaped clamp body having a pair of opposed parallel clamping arms 12' and 12". An adjustable holding screw 16 is associated with clamping arm 12' and an interior surface of clamping arm 12" has a compliant material plate 14 thereon for closely engaging the geometry of the surgical instrument 10. The clamping mechanism 12 is pivotably connected to the housing 2, 2' about a pivot axis defined by pin 22 that extends perpendicular to a longitudinal axis of the elongated housing 2 for adjusting the light angle of lighting device 20 relative to the distal end of the surgical instrument 10 so as to intersect the distal tip of the instrument. Those skilled in the art will readily appreciate that other mechanical clamping mechanisms may be employed to attach the lighting device to the surgical instrument, such as, for example, spring loaded clamps or the like. Alternatively, other types of attachment means could be employed, such as, for example, hook and loop type fasteners, adhesive tape or the like.

Figure 4:
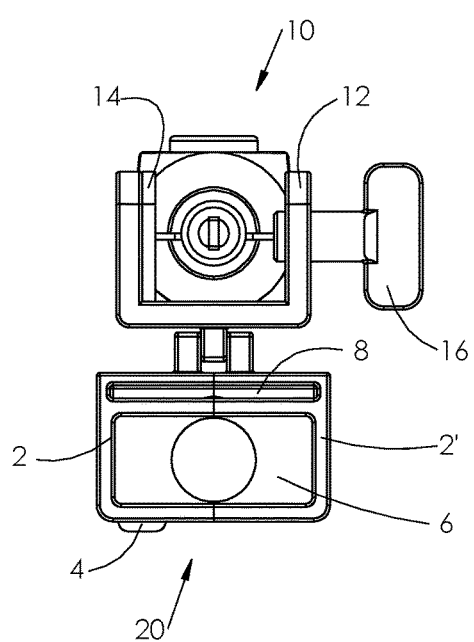
FIG. 4 is a front elevational view of the lighting device with internal smoke evacuation passage attached to a surgical instrument.
Figure 5:
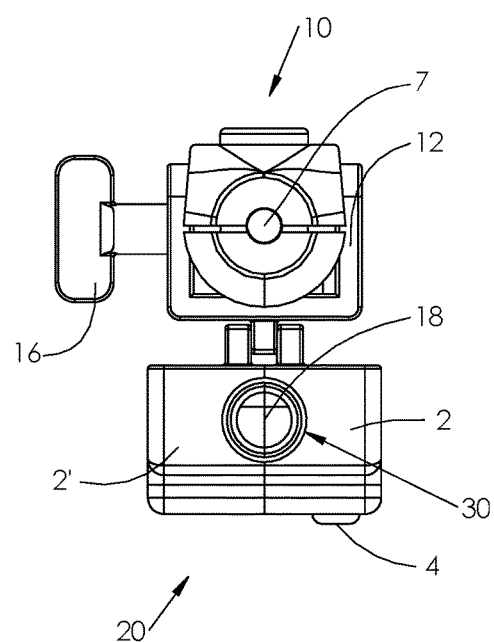
FIG. 5 is a rear elevational view of the lighting device with internal smoke evacuation passage attached to a surgical instrument.
Figure 6:
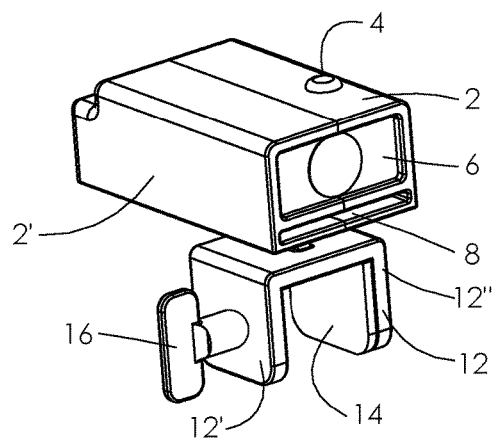
FIG. 6 is a frontal perspective view of the lighting device shown in FIG. 1.
Figure 7:
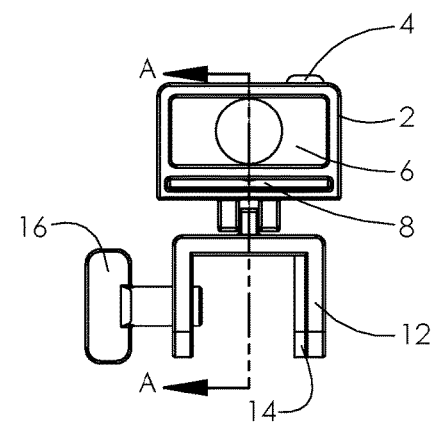
FIG. 7 is a front elevational view of the lighting device shown in FIG. 6.
Figure 8:
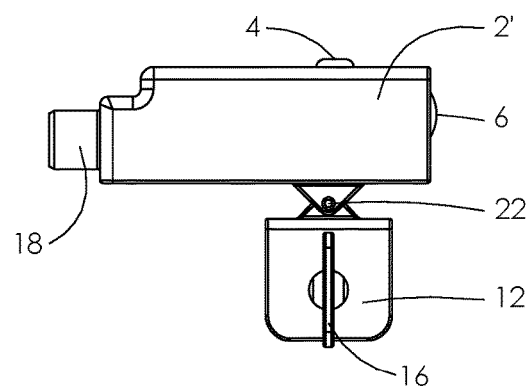
FIG. 8 is a side elevational view of the lighting device shown in FIG. 6.
Figure 9:
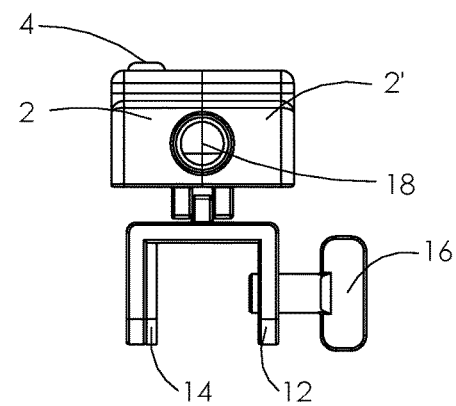
FIG. 9 is a rear elevational view of the lighting device shown in FIG. 6.
Figure 10:
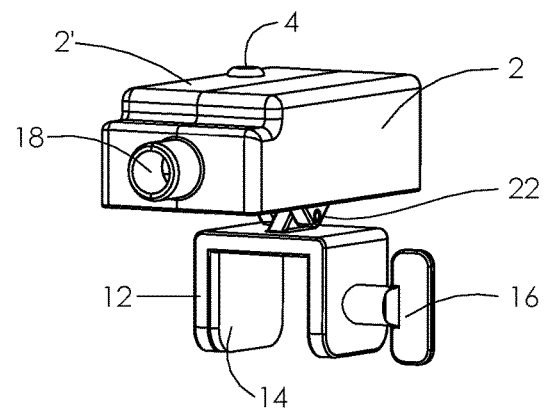
FIG. 10 is a posterior perspective view of the lighting device shown in FIG. 6.
Figure 11:
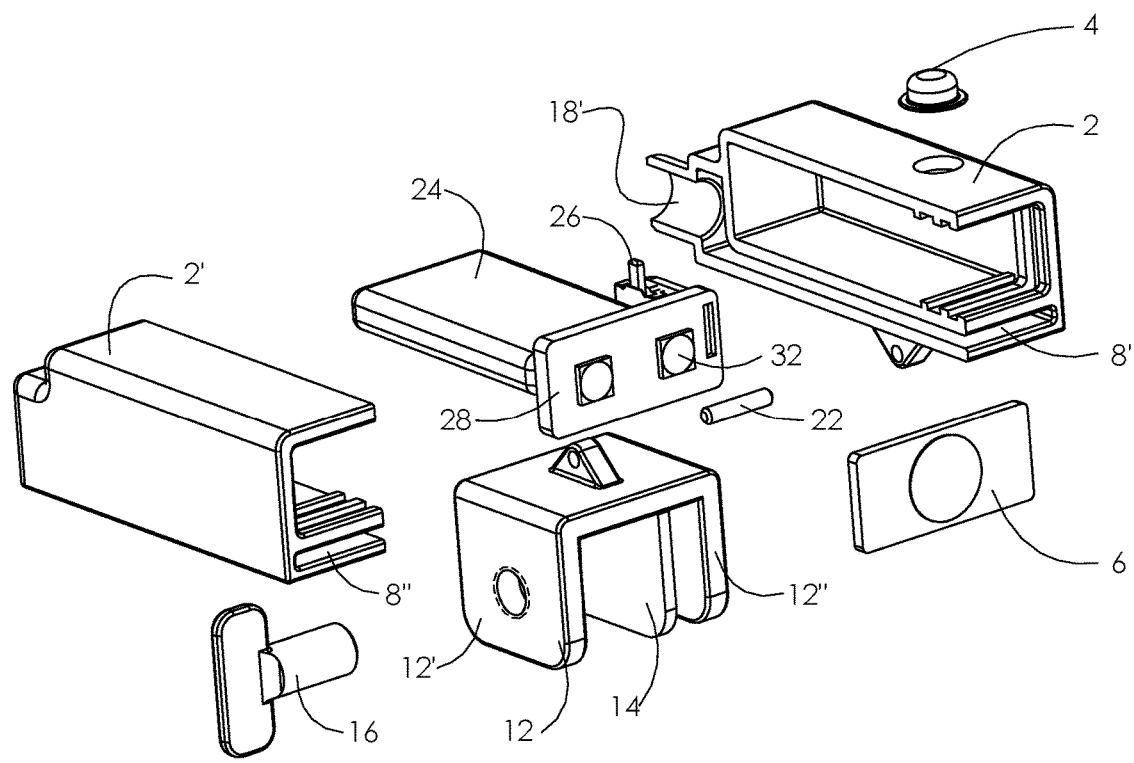
FIG. 11 is an exploded perspective view of the lighting device shown in FIG. 6, with parts separated for ease of illustration.

It is envisioned that a filter element could be located within the smoke evacuation passage 8 or within the smoke evacuation tube 30 to filter debris and/or contaminants from the air passing therethrough from the surgical site. It is also envisioned that the internal smoke evacuation passage 8 could have either a rectangular cross-sectional configuration as shown in FIG. 4, or the internal smoke evacuation passage could have a square cross-sectional configuration, an oval cross-sectional configuration, a circular cross-sectional configuration or any other shaped cross-sectional configuration that may be known and/or readily manufactured.

Figure 13:
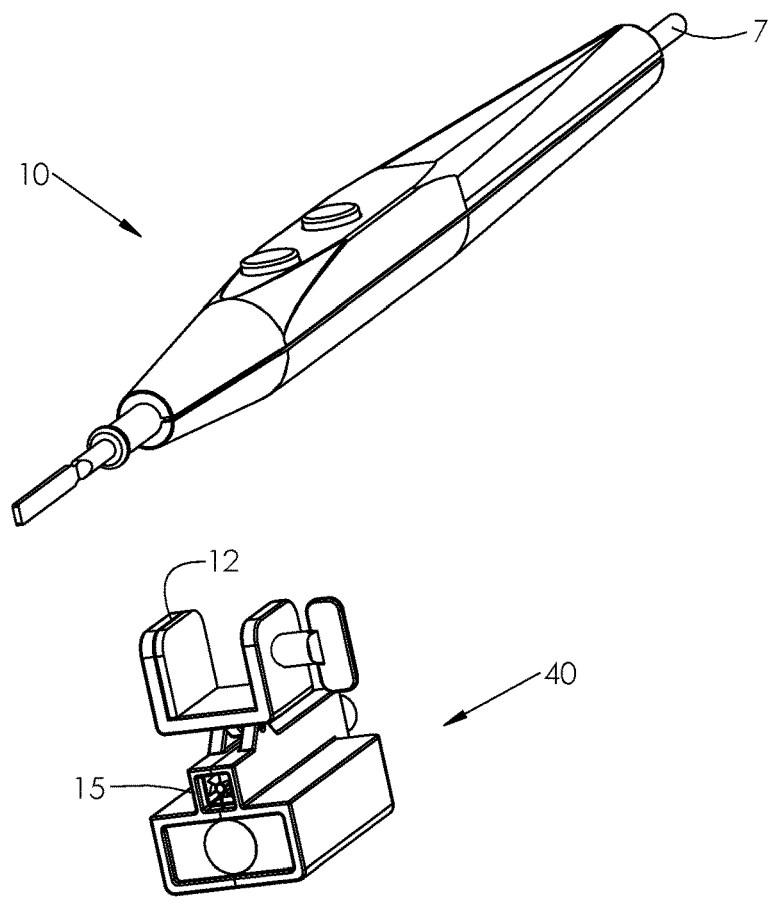
FIG. 13 is a perspective view of a lighting device with an internal smoke evacuation passage that includes an internal fan, which is separated from a surgical instrument to which it may be attached.
Figure 14:
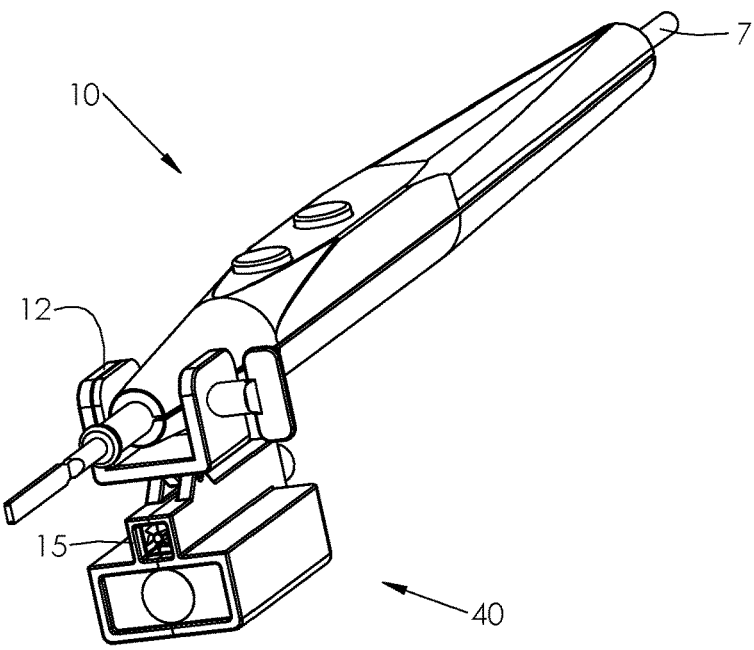
FIG. 14 is a perspective view of the lighting device of FIG. 13 attached to the surgical instrument.
Figure 15:
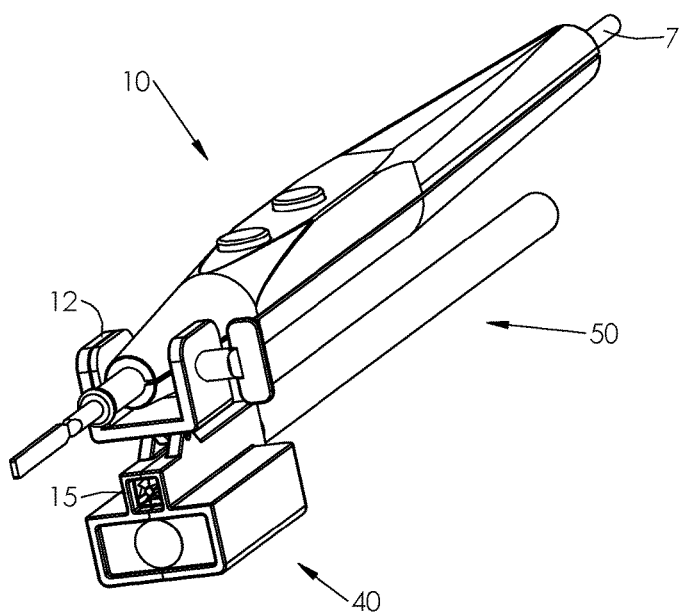
FIG. 15 is a perspective view of the lighting device and surgical instrument of FIG. 14, with smoke evacuation tubing connected thereto.
Figure 16:
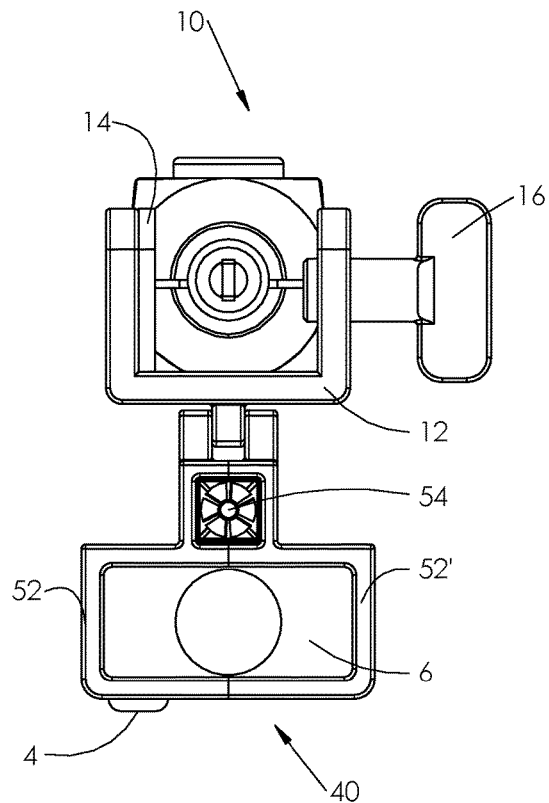
FIG. 16 is a front elevational view of the lighting device and surgical instrument of FIG. 15.
Figure 17:
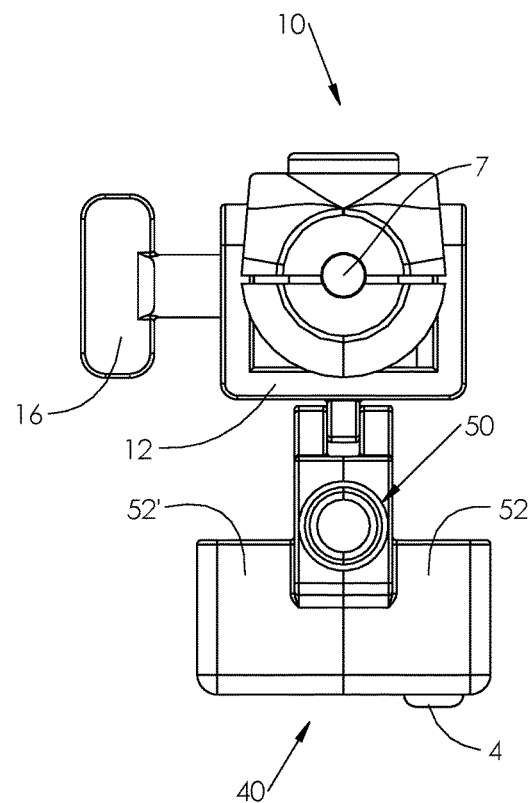
FIG. 17 is a rear elevational view of the lighting device and surgical instrument of FIG. 15.
Figure 18:
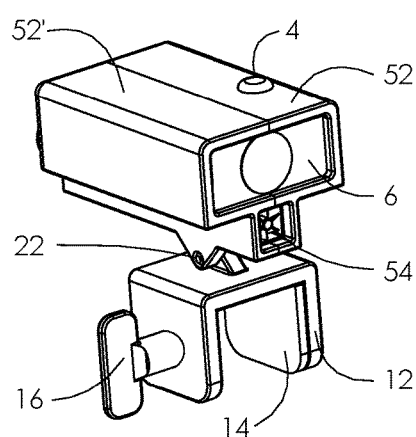
FIG. 18 is a frontal perspective view of the lighting device shown in FIG. 13.
Figure 19:
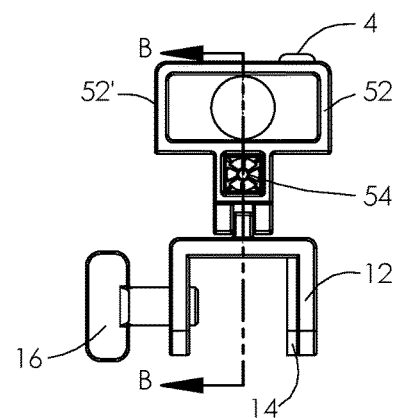
FIG. 19 is a front elevational view of the lighting device shown in FIG. 18.
Figure 20:
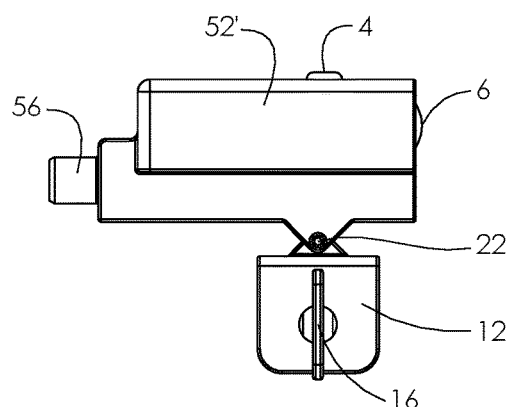
FIG. 20 is a side elevational view of the lighting device shown in FIG. 18.
Figure 21:
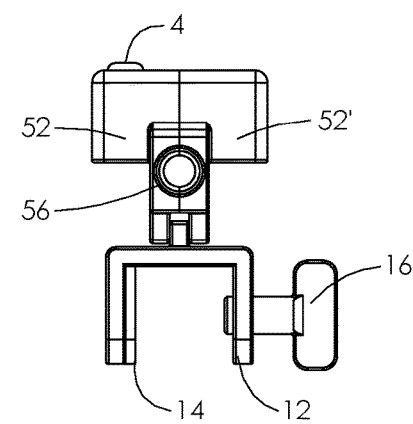
FIG. 21 is a rear elevational view of the lighting device shown in FIG. 18.
Figure 22:
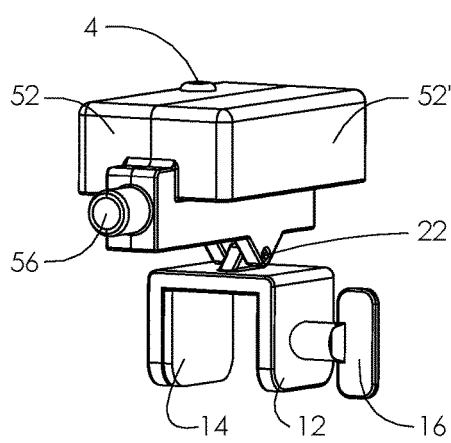
FIG. 22 is a posterior perspective view of the lighting device shown in FIG. 18.
Figure 23:
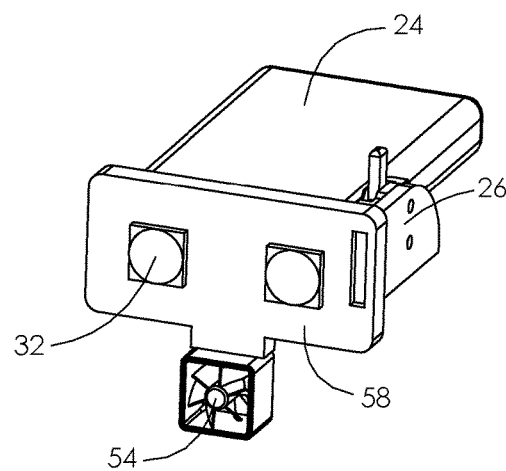
FIG. 23 is a perspective view of the printed circuit board, LEDs, switch and fan subassembly housed within the lighting device of FIG. 18.
Figure 24:
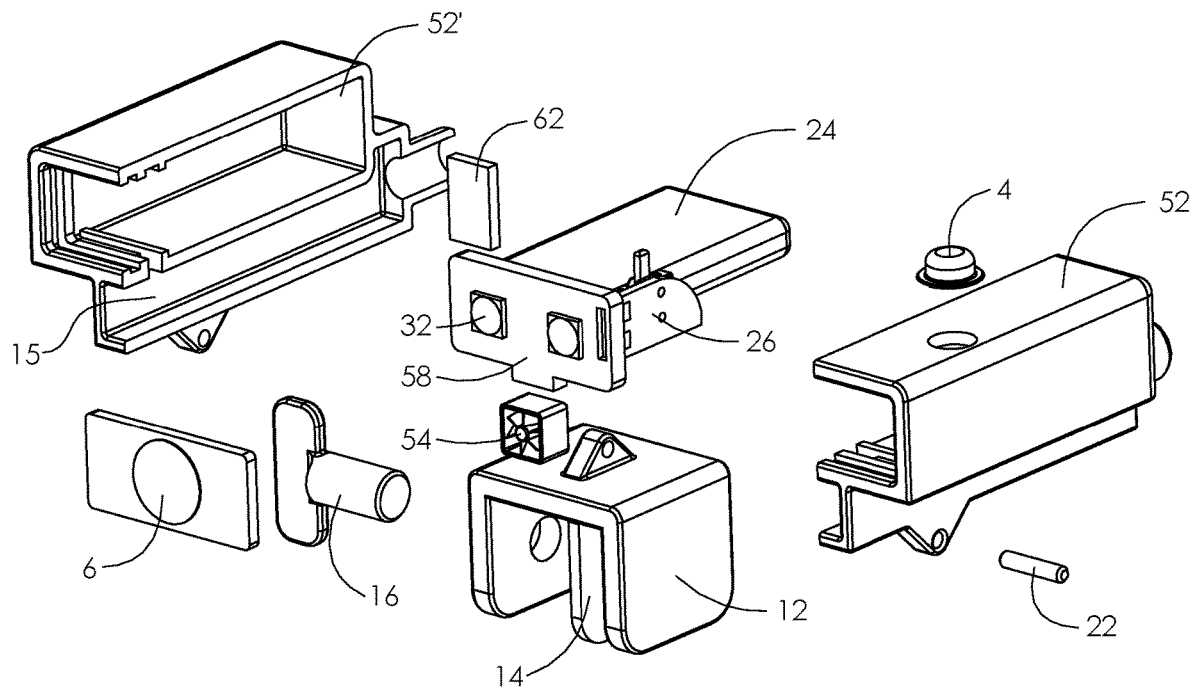
FIG. 24 is an exploded perspective view of the lighting device of FIG. 18, with parts separated for ease of illustration.

Referring now to FIGS. 13 and 14, there is illustrated another embodiment of a lighting device designated generally by reference numeral 40, which has an external smoke evacuation passage 15. The external smoke evacuation passage 15 is located outside of the main housing 52, 52' of the lighting device 40, separated from the interior chamber by an exterior wall of the housing. As shown in FIG. 15, an elongated smoke evacuation tube 50 connects the fitting 56 at the proximal end of the external smoke evacuation passage 15 of lighting device 40 to a source of suction such as pump or smoke evacuator (not shown).

Referring to FIGS. 18 through 25, lighting device 40 includes an adjustable clamping mechanism 12 that is substantially identical to the clamping mechanism 12 of lighting device 20, to facilitate the selective attachment of the lighting device 40 to the distal end portion of the surgical instrument 10. Lighting device 40 also includes a battery powered lighting assembly having a printed circuit board 58 with embedded LED light sources 32, a battery cell 24 and a switch 26 controlled by an actuation button 4. A lens 6 is positioned in a holding slots at the distal end of the housing 52, 52' adjacent the LED light sources 32.

Lighting device 40 also includes an internal rotatable fan 54 located near the distal inlet of the external smoke evacuation passage 15. The fan 54 may be configured to direct air flow from the smoke evacuation passage 15 or to draw air flow into the smoke evacuation passage 15. The fan 54 is electrically connected to the printed circuit board 58 and powered by the battery 24 of the lighting assembly contained within the two part rectangular housing 52, 52' of lighting device 40.

Those skilled in the art will readily appreciate that a plurality of fans or micro-fans can be positioned within the external smoke evacuation passage 15 of lighting device 40. It should also be appreciated that one or more fans could be similarly located in the internal smoke evacuation passage 8 of the lighting device 20, described above.

Figure 25:
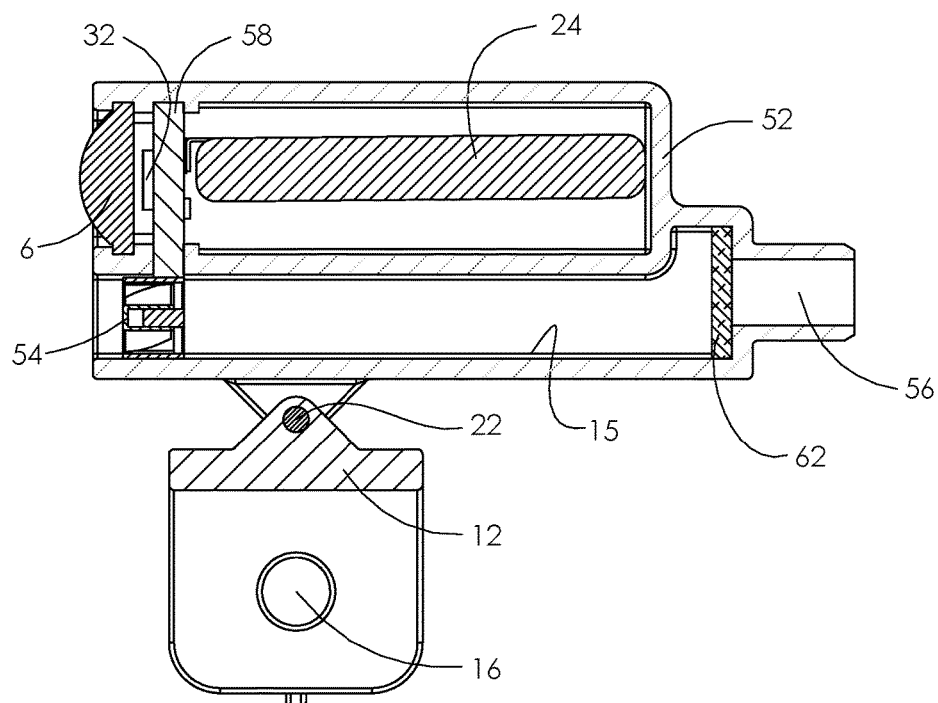
FIG. 25 is a cross-sectional view of the lighting device taken along line B-B of FIG. 19.
Figure 26:
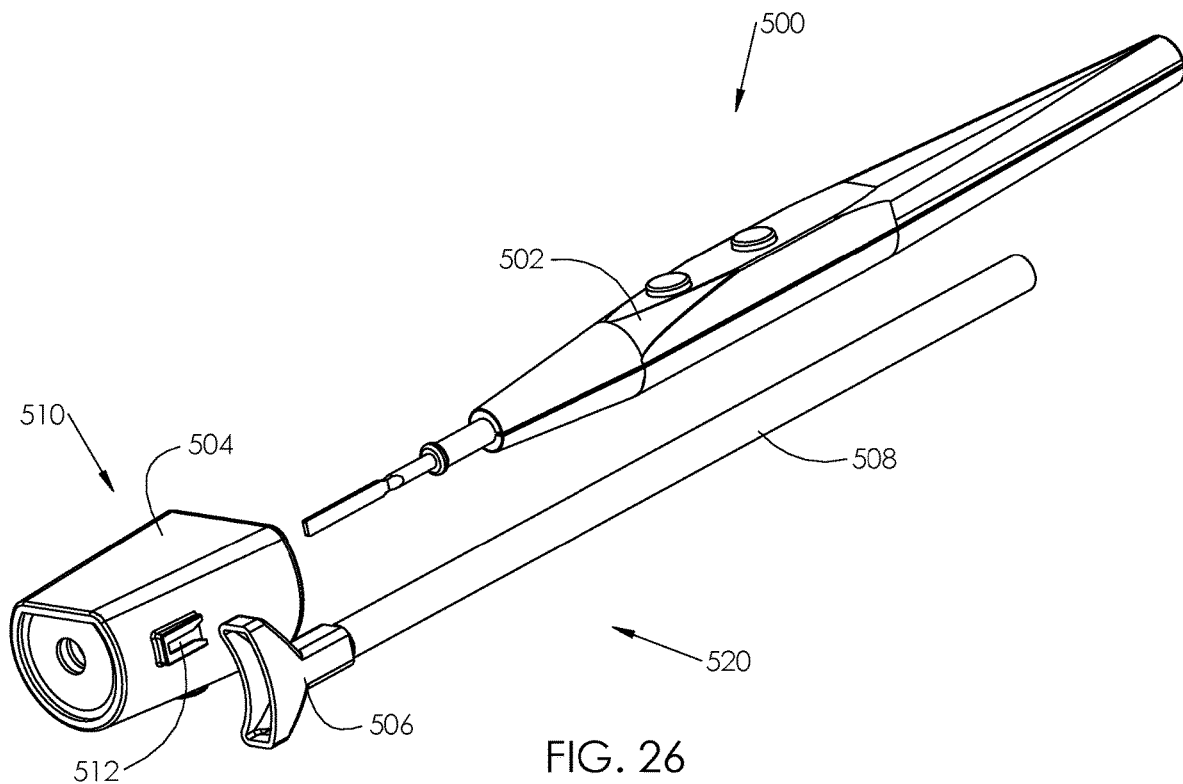
FIG. 26 is a perspective view of a surgical lighting device with an attachable smoke evacuation subassembly separated from a surgical instrument.

As best seen in FIG. 25, a filter element 62 is positioned near the proximal end portion of the external smoke evacuation passage 15 of lighting device 40. The filter element 62 may contain carbon or activated charcoal and may be a single or multi-layer composite and it can include mesh, paper or other filter layers, which can be hydrophobic.

Figure 27:
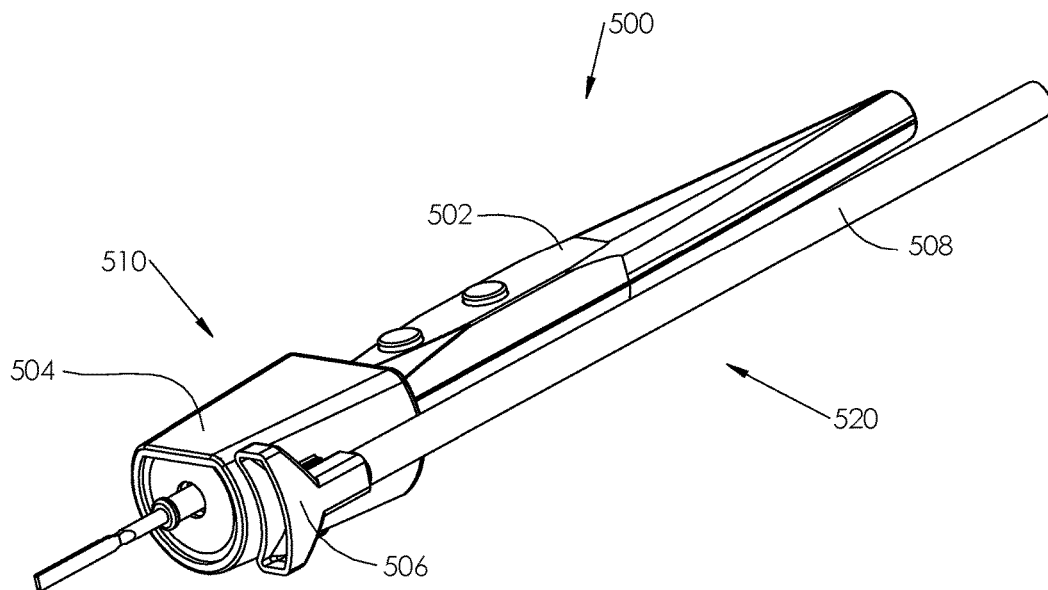
FIG. 27 is a perspective view of the surgical lighting device shown in FIG. 26 with the smoke evacuation subassembly attached thereto engaged on the distal end portion of the surgical instrument.
Figure 33:
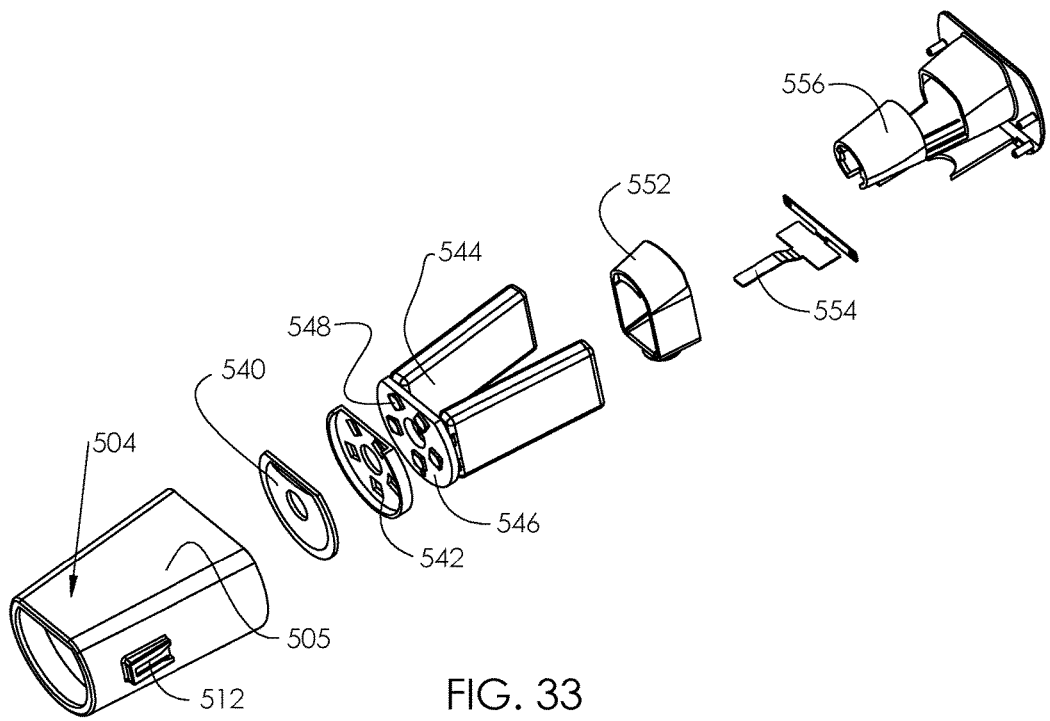
FIG. 33 is an exploded perspective view of the lighting device shown in FIG. 26.
Figure 34:
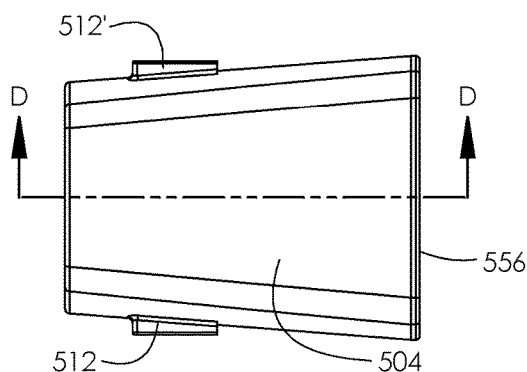
FIG. 34 is a top plan view of the lighting device shown in FIG. 26.
Figure 35:
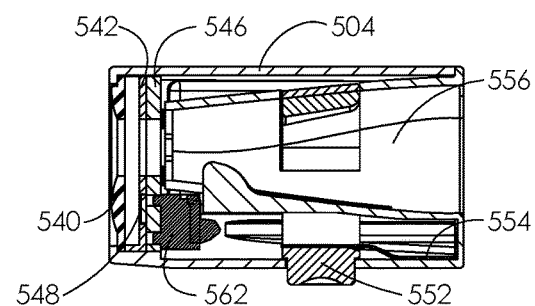
FIG. 35 is a cross-sectional view taken along line D-D of FIG. 34.
Figure 36:
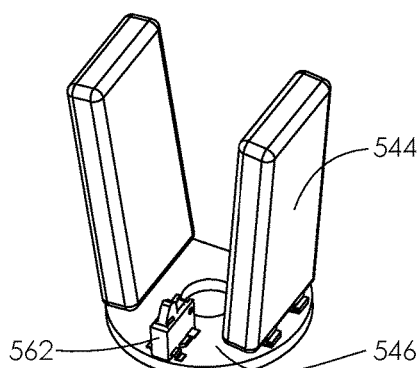
FIG. 36 is a perspective view of the subassembly with printed circuit board, battery, switch and LED housed in the lighting device shown in FIG. 26.
Figure 37:
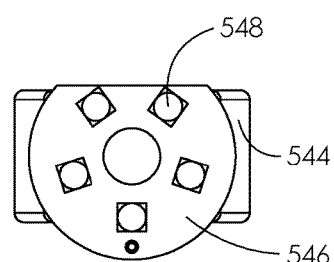
FIG. 37 is a front end view of the subassembly shown in FIG. 36.
Figure 38:
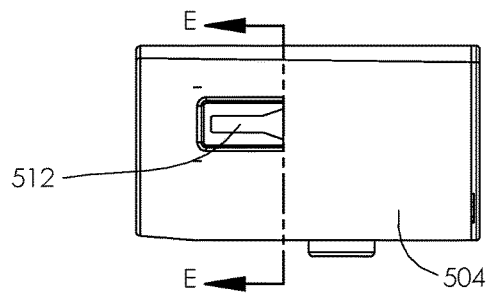
FIG. 38 is a side elevational view of lighting device shown in FIG. 26.
Figure 39:
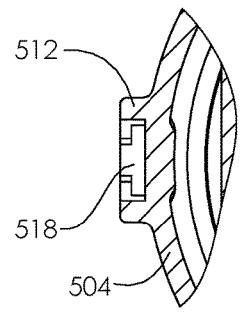
FIG. 39 is a partial cross-sectional view taken along line E-E of FIG. 38, illustrating the sliding mechanism for detachably connecting the smoke evacuation subassembly to the lighting device.
Figure 40:
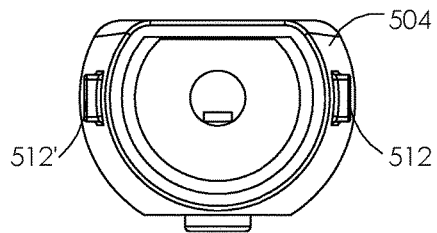
FIG. 40 is a front end view of the lighting device shown in FIG. 36.
Figure 41:
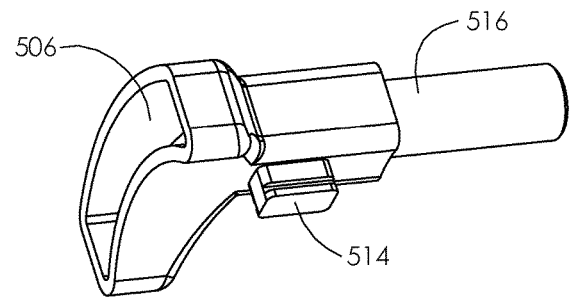
FIG. 41 is a perspective view of the smoke evacuation nozzle assembly shown in FIG. 26.
Figure 42:
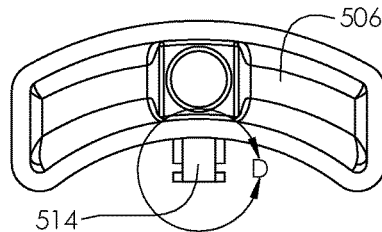
FIG. 42 is a front end view of the smoke evacuation nozzle assembly shown in FIG. 41.
Figure 43:
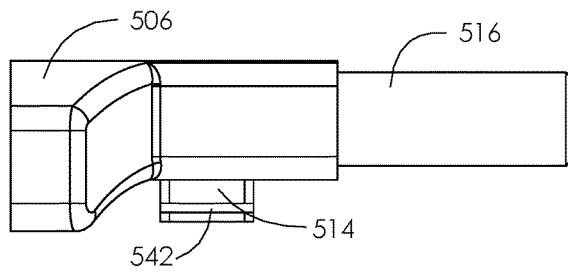
FIG. 43 is a side elevational view of the smoke evacuation nozzle assembly shown in FIG. 41.
Figure 44:
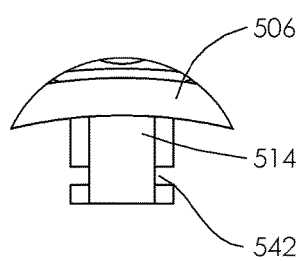
FIG. 44 is an enlarged localized view of the connective tongue shown in FIG. 42.
Figure 45:
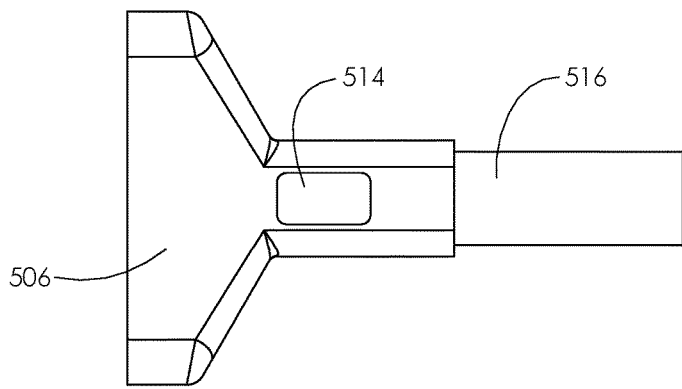
FIG. 45 is a bottom plan view of the smoke evacuation nozzle assembly shown in FIG. 41.
Figure 46:
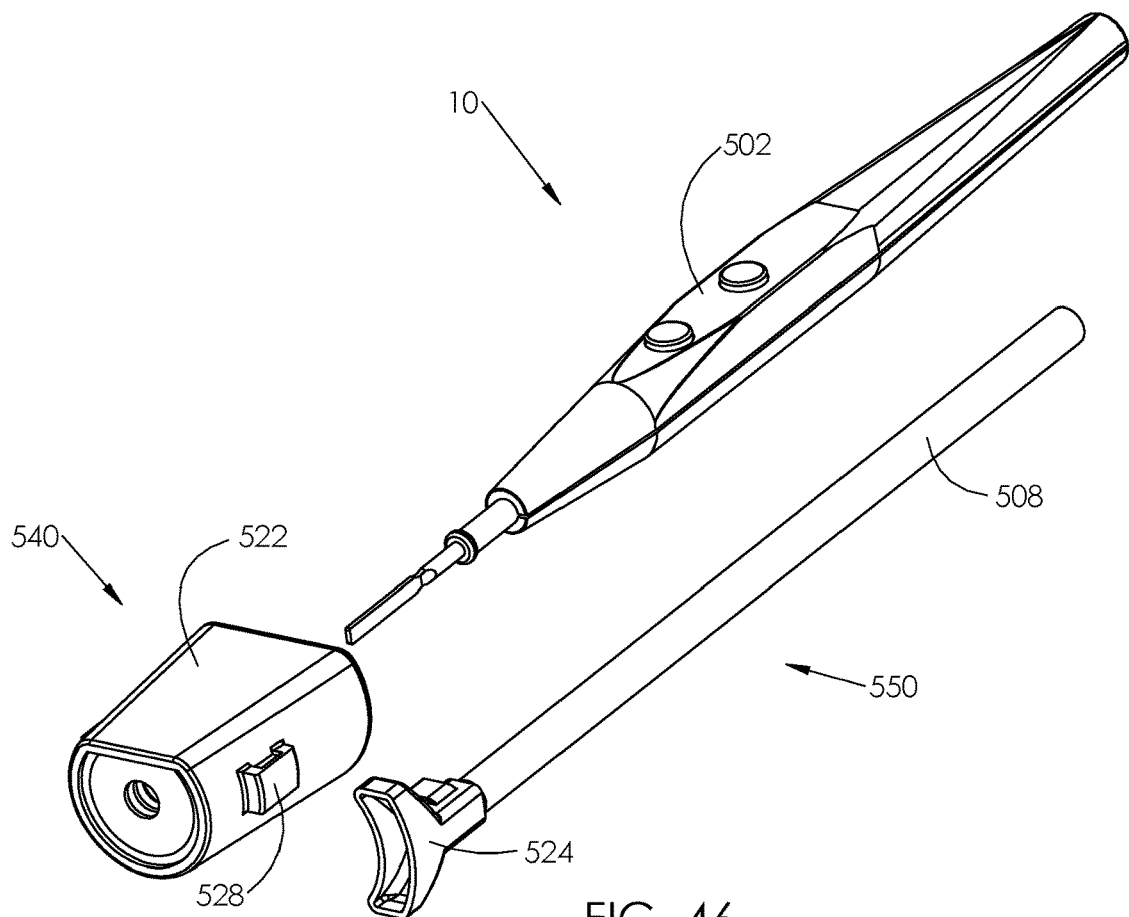
FIG. 46 is a perspective view of another surgical lighting device with a detachable attachable smoke evacuation subassembly separated from a surgical instrument.
Figure 47:
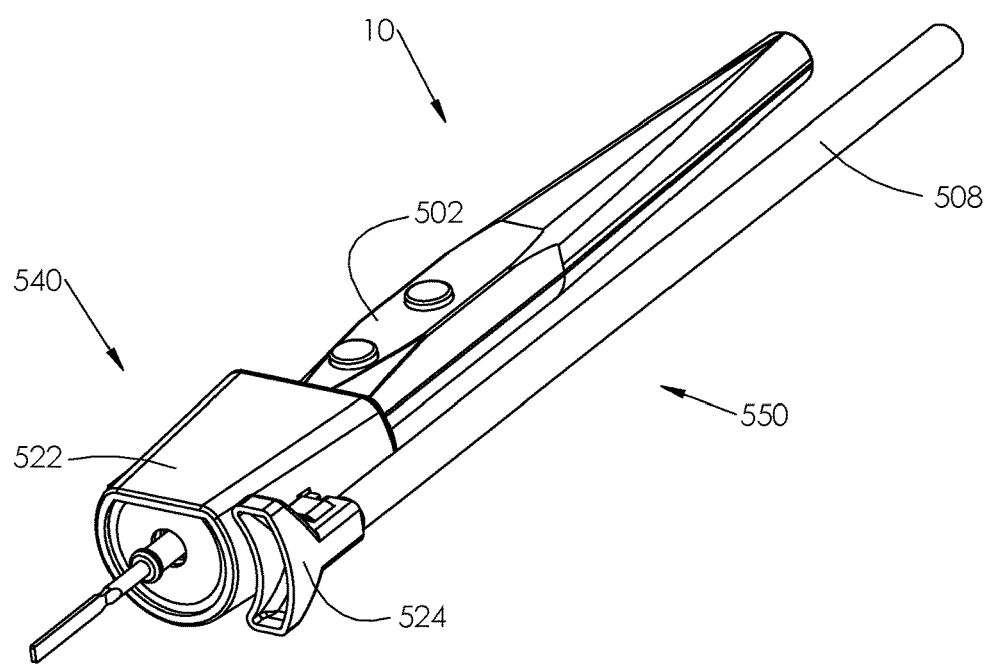
FIG. 47 is a perspective view of the surgical lighting device shown in FIG. 46 with the smoke evacuation subassembly attached thereto engaged on the distal end portion of the surgical instrument.

Referring now to FIGS. 26 through 45, there is illustrated another surgical lighting device designated by reference numeral 510 for use with a handheld electro surgical instrument 10, which cooperates with a detachable smoke evacuation assembly 520. As explained in more detail below, the lighting device 510 includes sliding engagement structures 512, 512' to facilitate the attachment of the smoke evacuation assembly 520 to the right side wall of the lighting device 510 as shown in FIGS. 27 and 28, or the left side wall of the lighting device 510 as shown in FIG. 29.

The smoke evacuation assembly 520 includes an inlet nozzle 506 defining a smoke evacuation passage located adjacent the distal end of the lighting device 510. An elongate smoke evacuation tube 508 extends from the proximal outlet 516 of the inlet nozzle 506 for communicating with a smoke evacuator or pump. As best seen in FIG. 32, a sliding connector 514 extends from a bottom surface of the inlet nozzle 506 for engaging with either one of the interfacing connectors 512 and 512' located on the right and left side walls of the lighting device 510 (see also FIG. 40). As shown for example in FIGS. 38 through 45, the sliding connector 514 includes a slotted tongue 522 for interfacing with a groove 518 formed in the sliding connectors 512, 512'.

Referring to FIGS. 33 through 37, the lighting device 510 includes a generally conical housing 504 having a substantially planar upper surface 505 to enable an unobstructed line of sight for the surgeon utilizing the surgical instrument 10. The housing 504 has an interior cavity that supports a lighting assembly, which includes a printed circuit board 546 having a plurality of circumferentially spaced apart embedded LED light sources 548, battery cells 544 and a switching mechanism 562. A lens 540 is positioned at the distal end of the housing 504 adjacent or near to the LED light sources 548. An engagement collar 552 with a cooperating spring 554 is operatively associated with the housing 504 of lighting device 510 for engaging the distal end portion of the surgical instrument 10 when it is received within the interior cavity 556 of the lighting device 510.

In use, when the distal end portion of the electrosurgical instrument 10 is inserted into the conical alignment sleeve 556 within interior cavity of the lighting device 510, the distal end portion of the instrument 10 will contact a flexible cantilevered foot that flexes downward to contact the switching mechanism 562, causing the LED light sources to illuminate. At such a time, the distal end portion of the instrument will be mechanically retained by the spring biased engagement collar 552. Thereupon, a surgeon using the instrument 10 will be able to incise tissue, while illuminating the surgical site and removing smoke therefrom with the lighting device 510 and its smoke evacuation assembly 520 attached on either side thereof.

Figure 48:
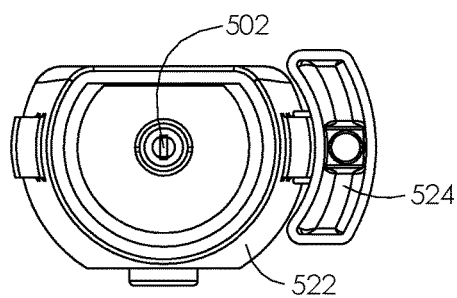
FIG. 48 is a front elevational view of the assembly shown in FIG. 47 illustrating a left side attachment.
Figure 49:
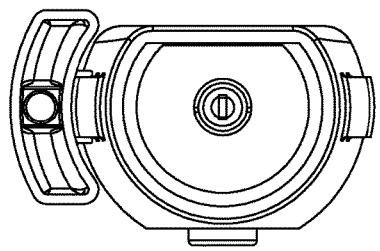
FIG. 49 is a front elevational view of the assembly shown in FIG. 47 illustrating a right side attachment.
Figure 50:
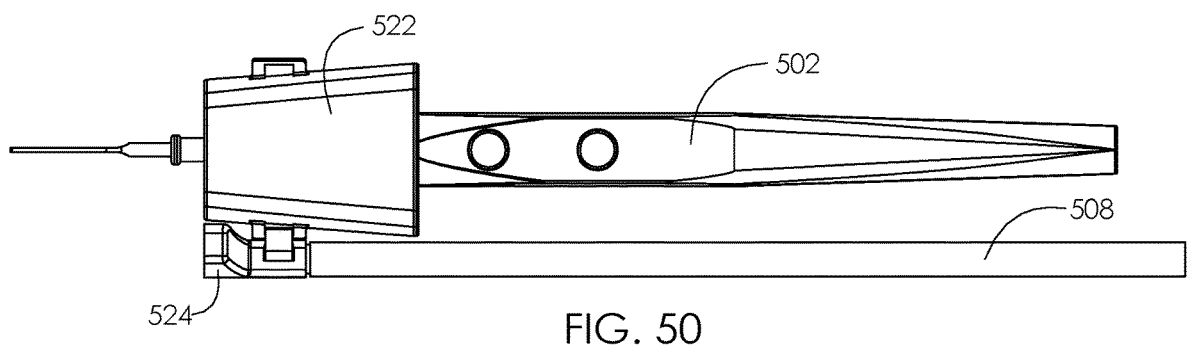
FIG. 50 is a top plan view of the assembly shown in FIG. 47.
Figure 51:
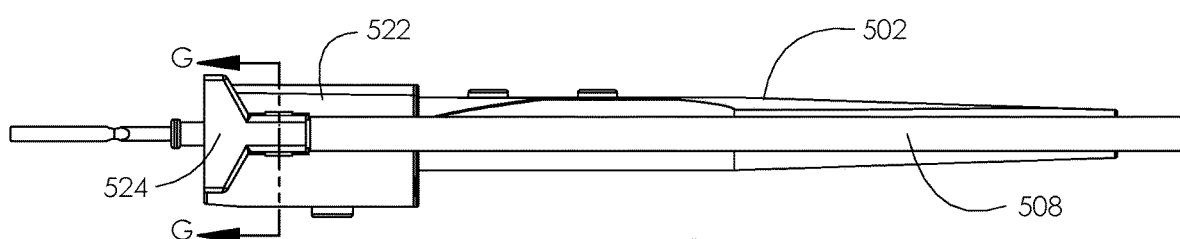
FIG. 51 is a right side elevational view of the assembly shown in FIG. 47.

Referring now to FIGS. 46 through 60, there is illustrated yet another surgical lighting device designated by reference numeral 530 for use with a handheld electrosurgical instrument 10, which cooperates with a detachable smoke evacuation assembly 550. As explained in more detail below, housing 532 of lighting device 530 includes snapping engagement structures 528, 528' to facilitate the attachment of the smoke evacuation assembly 550 to the right side wall of the housing 532, as shown in FIG. 48, or the left side wall of the housing 532, as shown in FIG. 49.

Figure 52:
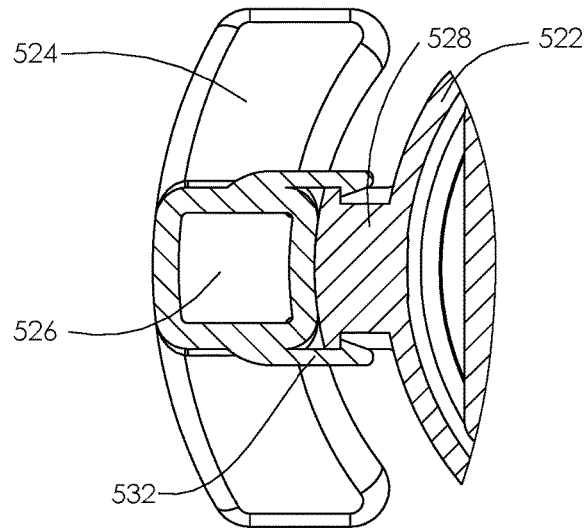
FIG. 52 is a partial section view taken along line G-G of FIG. 51.
Figure 53:
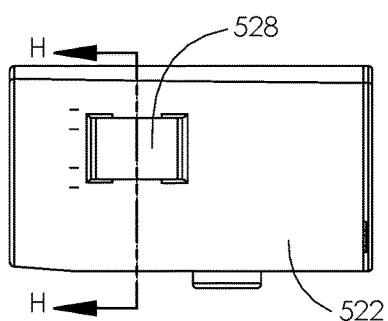
FIG. 53 is a right side elevational view of lighting device shown in FIG. 46.
Figure 54:
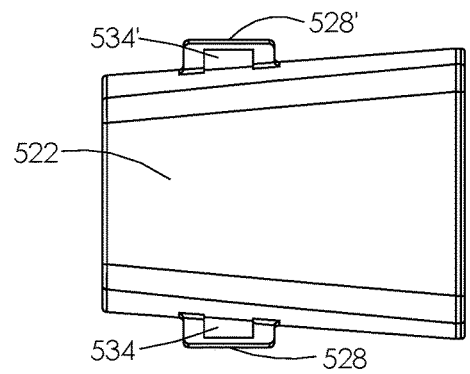
FIG. 54 is a top plan view of the lighting device shown in FIG. 46.
Figure 55:
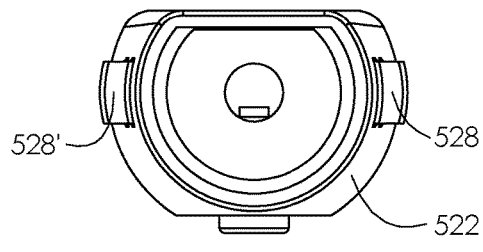
FIG. 55 is a front end view of the subassembly shown in FIG. 46.
Figure 56:
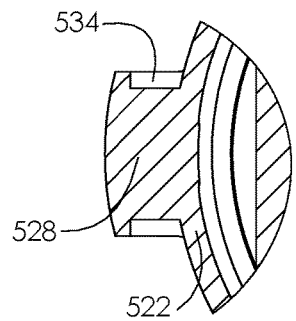
FIG. 56 is a partial cross-sectional view taken along line H-H of FIG. 53.
Figure 57:
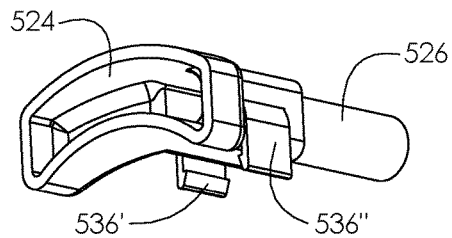
FIG. 57 is a perspective view of the smoke evacuation nozzle assembly shown in FIG. 46.
Figure 58:
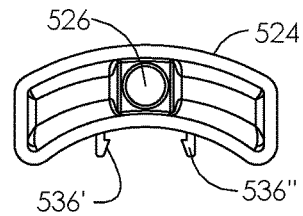
FIG. 58 is a front end view of the smoke evacuation nozzle assembly shown in FIG. 57.
Figure 59:
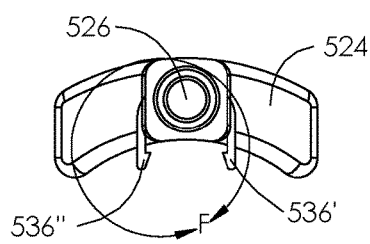
FIG. 59 is a rear end view of the smoke evacuation nozzle assembly shown in FIG. 57.
Figure 60:
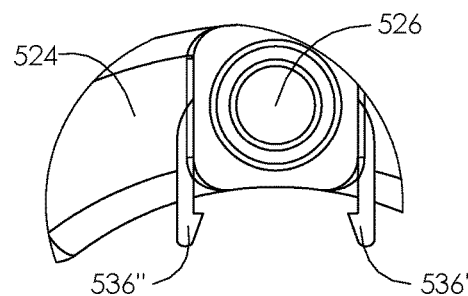
FIG. 60 is an enlarged localized view of the connective arms shown in FIG. 59.

The smoke evacuation assembly 550 includes an inlet nozzle 524 defining a smoke evacuation passage located adjacent to the distal end of the housing 532. An elongated smoke evacuation tube 508 extends from the proximal outlet 526 of the inlet nozzle 524 for communicating with a smoke evacuator or pump. As best seen in FIG. 52, a snapping connector 536 extends from a bottom surface of the inlet nozzle 524 for engaging with the snapping connectors 528 and 528' on the right and left side walls of the housing 532 of lighting device 530. As shown for example in FIGS. 53 through 60, the snapping connector 536 includes a pair of deflectable legs 536' and 536" for interfacing with or otherwise engaging complementary grooves 534, 534' in the sliding connectors 528, 528'.

Referring to FIGS. 61 through 70, there is illustrated another embodiment of a detachable smoke evacuation assembly designated generally by reference numeral 560 for use with lighting device 510. Smoke evacuation assembly 560 includes an inlet nozzle 506 and an elongated smoke evacuation tube 566. The inlet nozzle 506 is adapted and configured for attachment to the housing 504 of lighting device 510 as explained in detail above.

Figure 65:
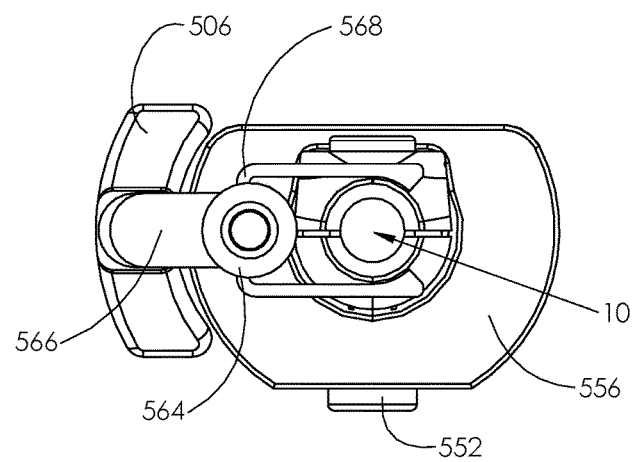
FIG. 65 is a rear end view of the assembly shown in FIG. 62.
Figure 66:
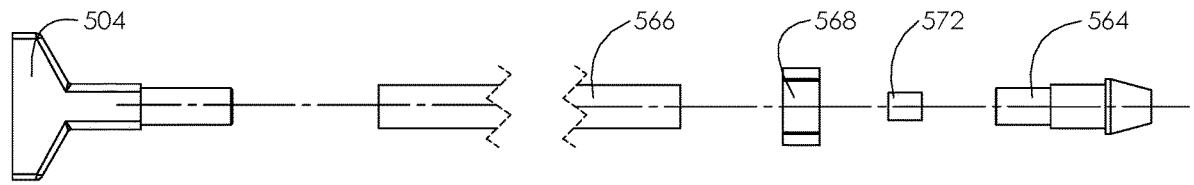
FIG. 66 is an exploded side elevational view of the smoke evacuation passage shown in FIG. 62, which includes the nozzle assembly, smoke evacuation tube, engagement clip and barbed connector.
Figure 67:
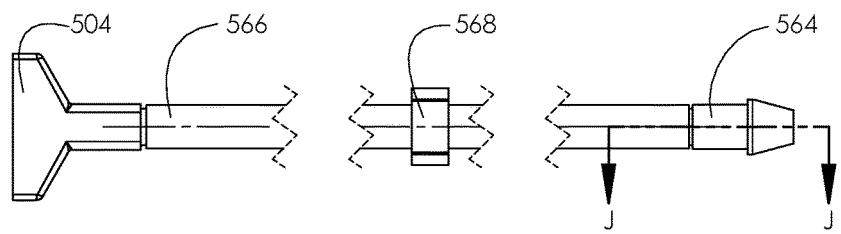
FIG. 67 is an assembled side elevational view of the smoke evacuation passage shown in FIG. 62.
Figure 69:
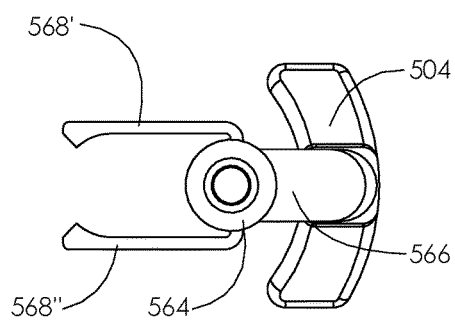
FIG. 69 is a rear end view of the smoke evacuation passage shown in FIG. 62.
Figure 70:
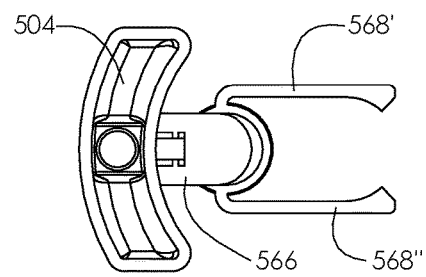
FIG. 70 is a front end view of the smoke evacuation passage shown in FIG. 62.
Figure 71:
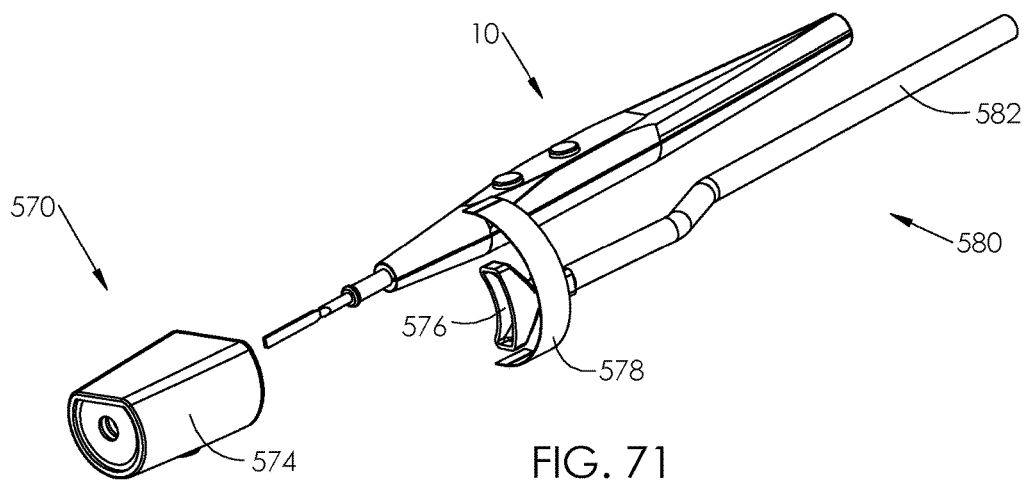
FIG. 71 is a perspective view similar to that of FIG. 46, wherein the nozzle assembly includes an adhesive strip for securing the smoke evacuation passage to the lighting device, which is shown separated from a surgical instrument.
Figure 72:
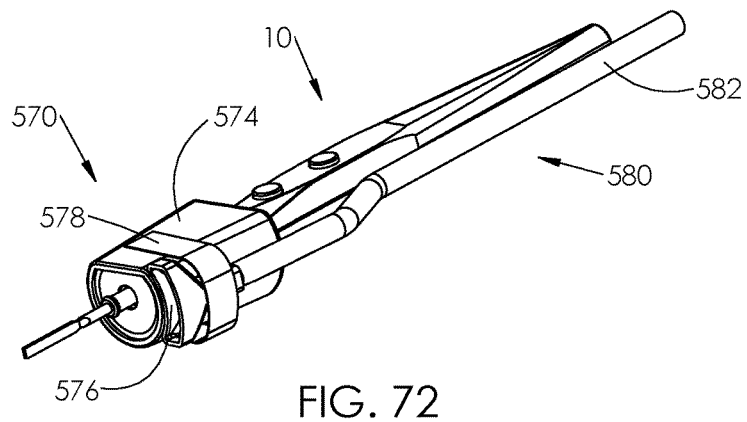
FIG. 72 is a perspective as in FIG. 71, with the lighting device positioned on the distal end portion of the surgical instrument and with the nozzle assembly of the smoke evacuation passage attached to the lighting device with the adhesive strip.
Figure 73:
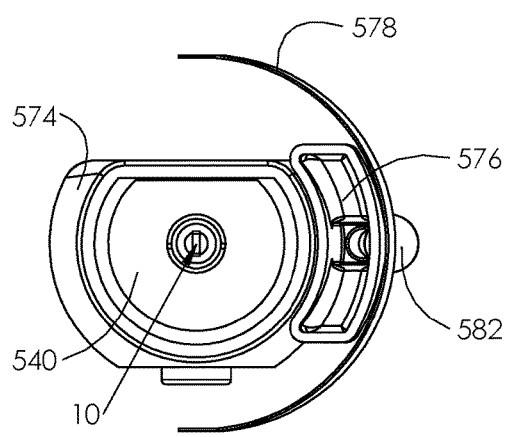
FIG. 73 is a front end view of the assembly shown in FIG. 72 with the adhesive strip in an unsecured condition.
Figure 74:
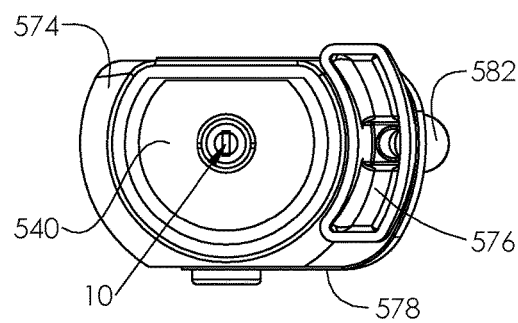
FIG. 74 is a front end view of the assembly shown in FIG. 72 with the adhesive strip in a secured condition.
Figure 75:
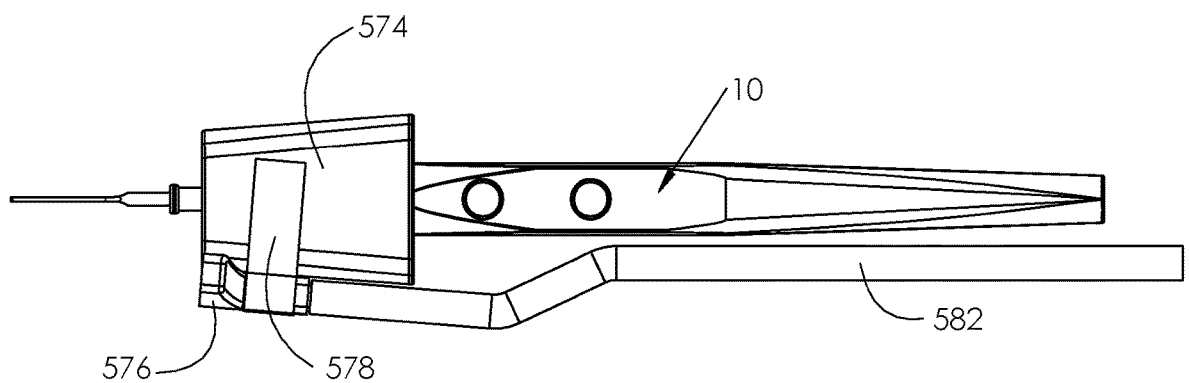
FIG. 75 is a top plan view of the assembly shown in FIG. 72 with the adhesive strip in a secured condition.
Figure 76:
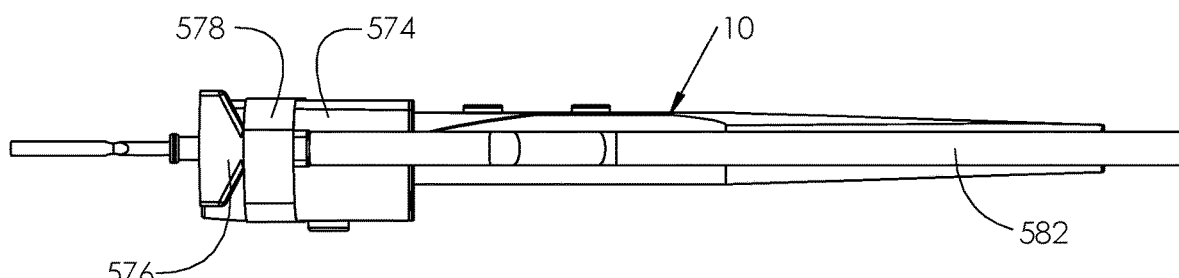
FIG. 76 is a right side elevational view of the assembly shown in FIG. 72 with the adhesive strip in a secured condition.
Figure 77:
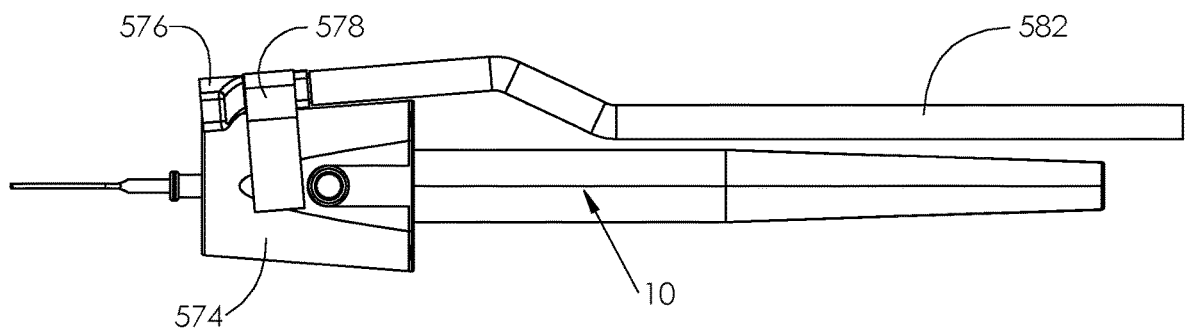
FIG. 77 is a bottom plan view of the assembly shown in FIG. 72 with the adhesive strip in a secured condition.
Figure 78:
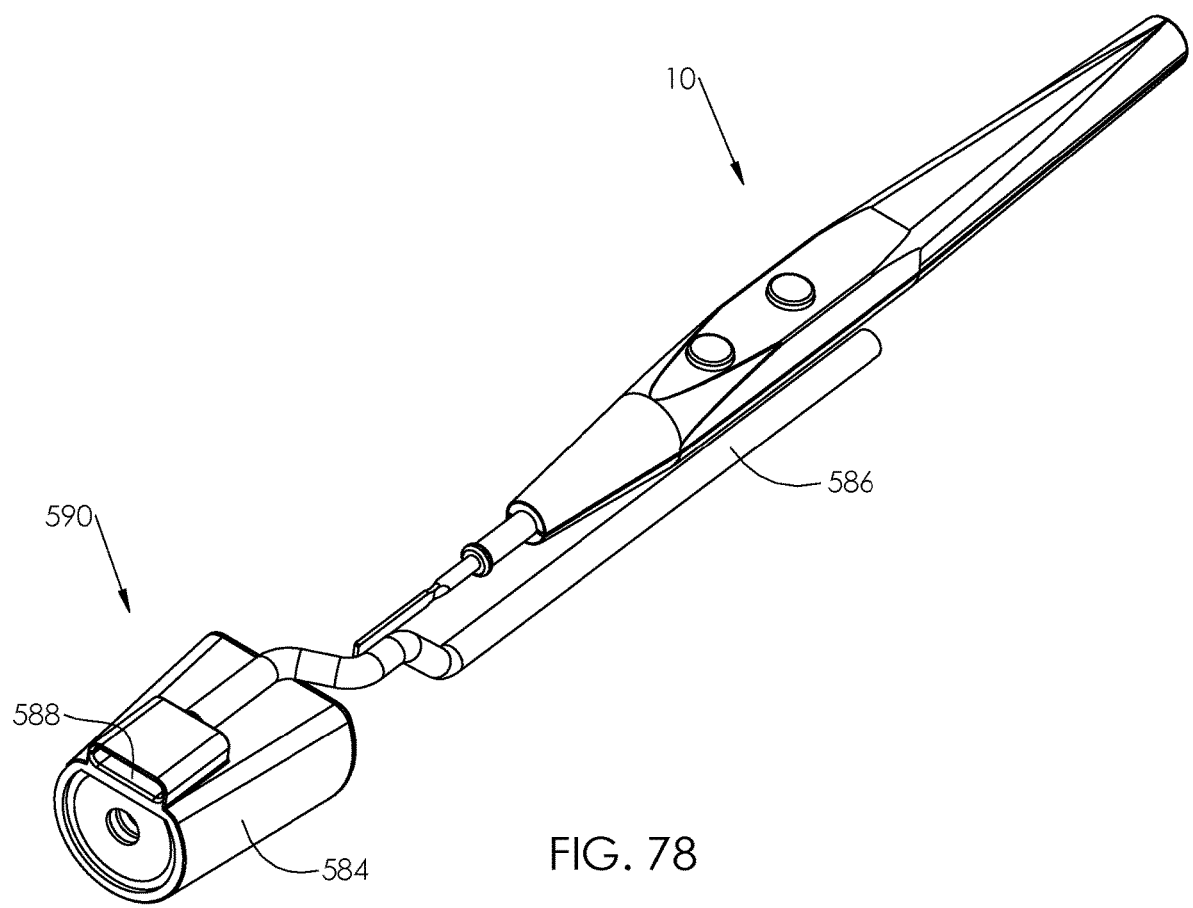
FIG. 78 is a perspective view of a lighting device with an external smoke evacuation passage, which is separated from a surgical instrument to which it may be attached.
Figure 79:
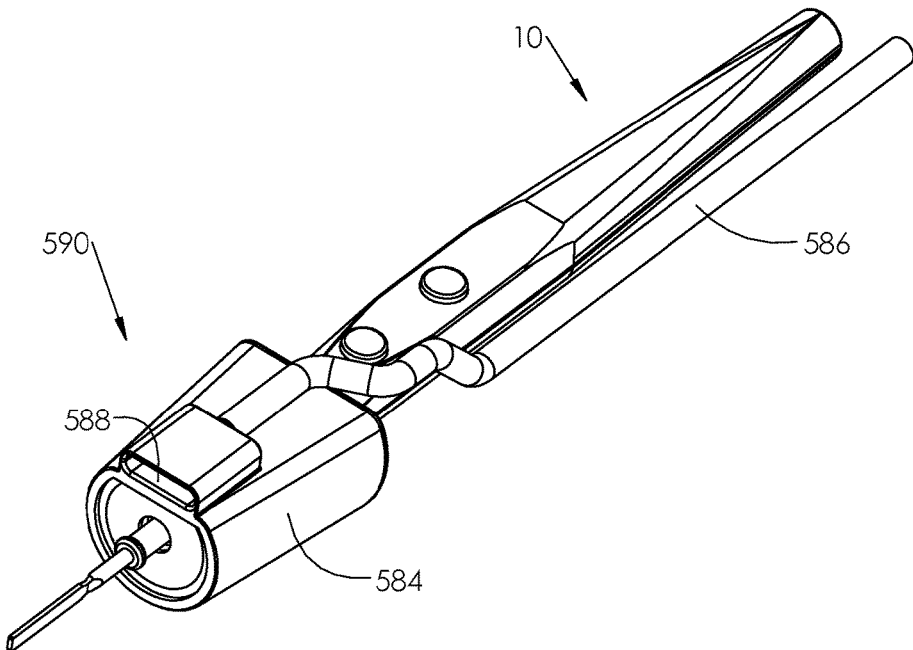
FIG. 79 is a perspective view of the lighting device with an external smoke evacuation passage attached to the distal end portion of the surgical instrument shown in FIG. 78.
Figure 80:
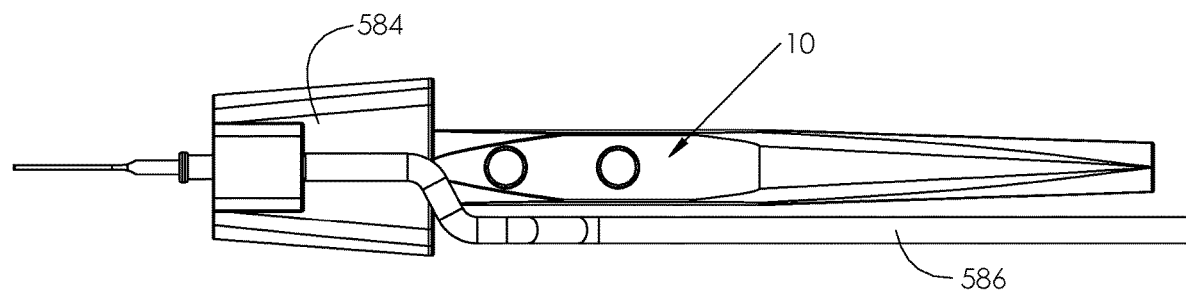
FIG. 80 is a top plan view of the assembly shown in FIG. 79.
Figure 81:
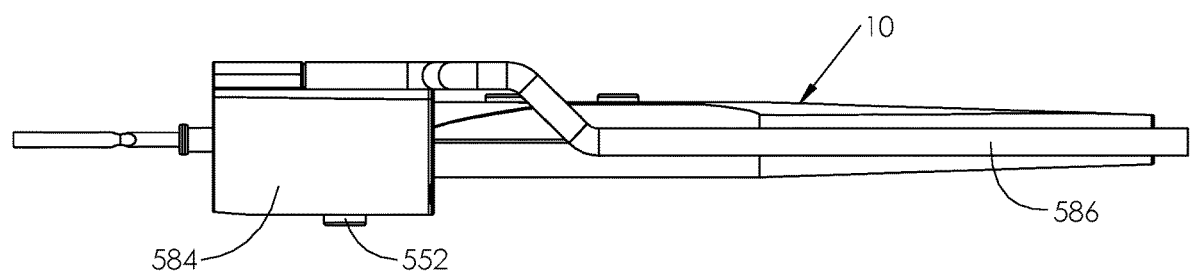
FIG. 81 is a right side elevational view of the assembly shown in FIG. 79.
Figure 82:
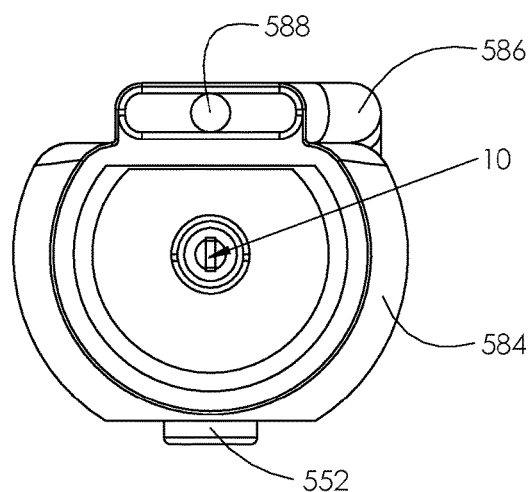
FIG. 82 is a front end view of the assembly shown in FIG. 79.

A retention clip 568 is operatively positioned along the length of the tube 566, as shown in FIGS. 69 and 70, for selectively engaging a proximal end portion of the surgical instrument 10, employed with surgical instrument 10 (see FIG. 65). The retention clip 568 includes a pair of barbed retention legs 568' and 568" that serve to retain the tube 566 in a fixed location so that it does not interfere with the performance of a surgical procedure.

Figure 68:
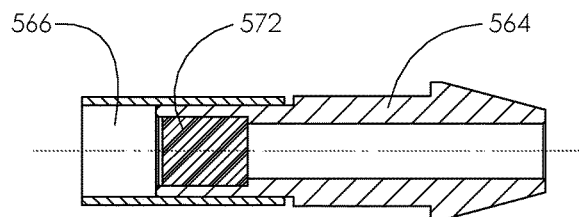
FIG. 68 is a cross-sectional view of barbed connector taken along line K-K of FIG. 67 illustrating a possible location for a filter element.

A barbed connector fitting 564 is operatively positioned at the proximal end of the smoke evacuation tube 566 for communicating with a smoke evacuator or pump. Other types of connectors or fitting could also be utilized. As best seen in FIG. 68, a filter element 572 is positioned with the central passageway of the connector fitting 564 for filtering the smoke filled air passing therethrough under suction by the smoke evacuator or pump. The filter element 572 can be formed from carbon, activated carbon or a similar filtration media.

Referring to FIGS. 71 through 77, there is illustrated another embodiment of a detachable smoke evacuation assembly 580 for use with a lighting device 570 employed with a handheld surgical instrument 10. The smoke evacuation assembly 580 includes an inlet nozzle 576, an elongated smoke evacuation tube 582 and an adhesive strip 578. The adhesive strip 578 is dimensioned and configured to extend at least partially around the periphery of the housing 574 of lighting device 570 and securely fasten the nozzle 576 thereto.

Figure 83:
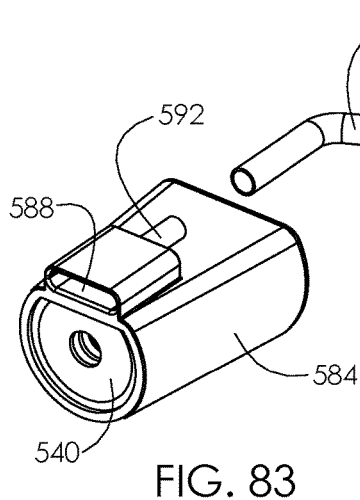
FIG. 83 is a perspective view of the lighting device shown in FIG. 79, with the smoke evacuation tubing disconnected from the external smoke evacuation passage.
Figure 84:
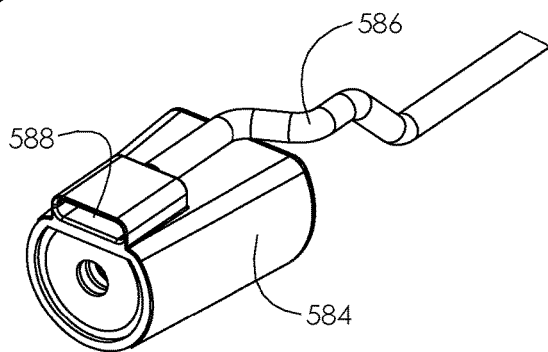
FIG. 84 is a perspective view of the lighting device shown in FIG. 79, with the smoke evacuation tubing connected to the external smoke evacuation passage.
Figure 85:
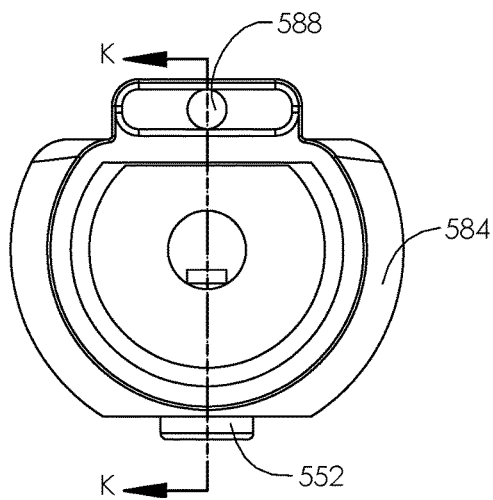
FIG. 85 is a front end view of the lighting device shown in FIG. 84.

Referring now to FIGS. 78 through 86, there is illustrated another embodiment of a lighting device 590 that has an external smoke evacuation passage 588 formed integral with the housing 584 of the lighting device 590 for use in conjunction with a handheld electrosurgical instrument 10. The smoke evacuation passage 588, which can have any type of cross-sectional configuration, but as shown here has a generally oval cross-sectional configuration and extends from an inlet adjacent to the distal end of the housing 584 to an outlet 592 adjacent to or nearby the proximal end of the housing 584. A smoke evacuation tube 586 connects with the outlet 592 to enable communication with a smoke evacuator or pump, as best seen in FIG. 83.

Figure 86:
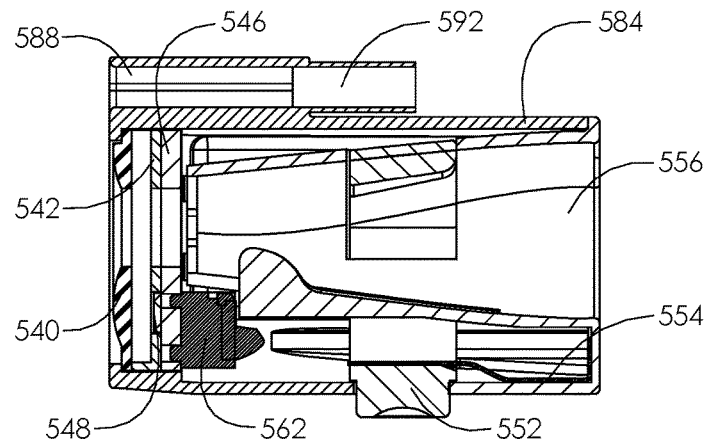
FIG. 86 is a cross-sectional view taken along line L-L of FIG. 85.

As best seen in FIG. 86, lighting device 590 has an interior cavity with a conical alignment sleeve 556 and a lighting assembly which includes a printed circuit board 546 having a plurality of embedded LED light sources 548, battery cells (not shown) and a switching mechanism 562. A lens 540 is positioned at the distal end of housing 584 and a spacer 542 is located between the lens 540 and the light sources 548 on the printed circuit board 546. An engagement collar 552 with a cooperating spring 554 is operatively associated with the interior cavity 556 of the lighting device 584 for engaging the distal end portion of the surgical instrument 10 when it is received within the interior cavity 556 of the lighting device 590.

In use, when the distal end portion of the electrosurgical instrument 10 is inserted into the sleeve 556 within the interior cavity of the lighting device 590, the distal end portion of the instrument 10 will contact a flexible member and push it downwardly to engage the switching mechanism 562, causing the LED light sources 548 to illuminate. At such a time, the distal end portion of the instrument 10 will be mechanically retained by the spring biased engagement collar 552. Thereupon, a surgeon employing the electrosurgical instrument 10 will be able to incise tissue while illuminating the surgical site and removing smoke therefrom, using the lighting device 590 and its external smoke evacuation passage 588 formed integral with housing 584.

Figure 87:
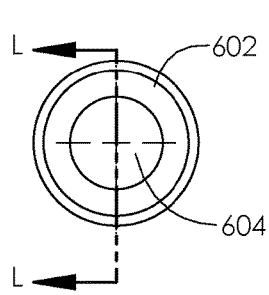
FIG. 87 is a front end view of a tube-shaped smoke evacuation inlet nozzle.
Figure 88:
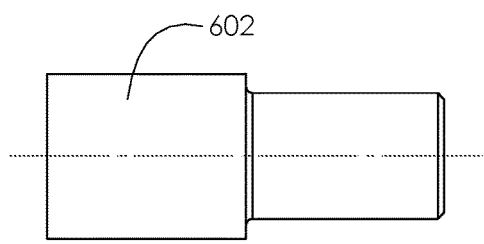
FIG. 88 is a side elevational view of inlet nozzle shown in FIG. 87.
Figure 89:
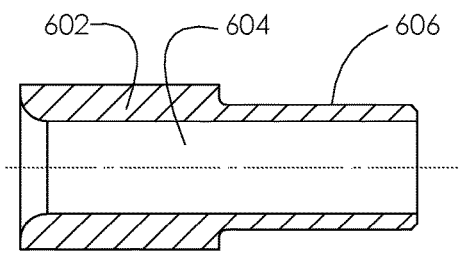
FIG. 89 is a cross-sectional view taken along line M-M of FIG. 87.
Figure 90:
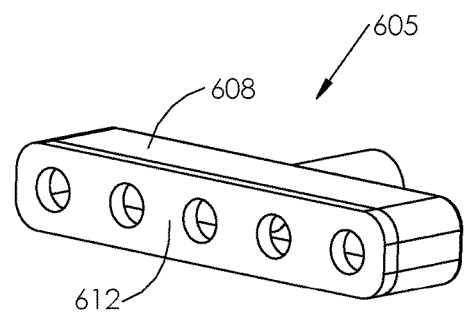
FIG. 90 is a perspective view of a multi-orifice smoke evacuation inlet nozzle configured to distribute suction across a distance to better pull surgical smoke covering a wider area in the surgical field.
Figure 91:
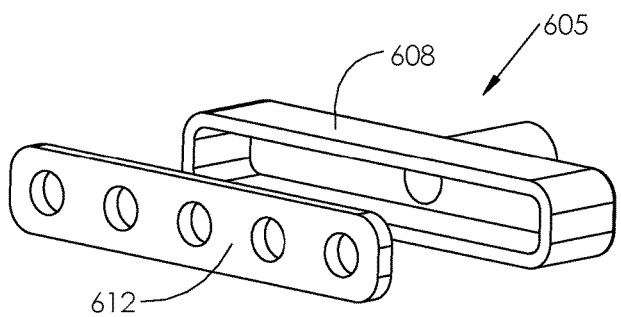
FIG. 91 is an exploded perspective view of the inlet nozzle shown in FIG. 90.
Figure 92:
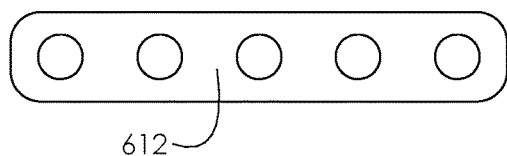
FIG. 92 is a front end view of the inlet nozzle shown in FIG. 90.
Figure 93:
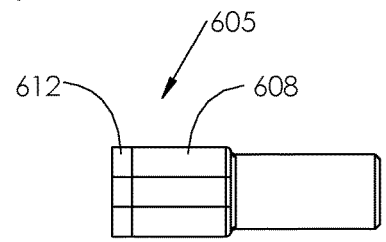
FIG. 93 is a side end view of the inlet nozzle shown in FIG. 90.
Figure 94:
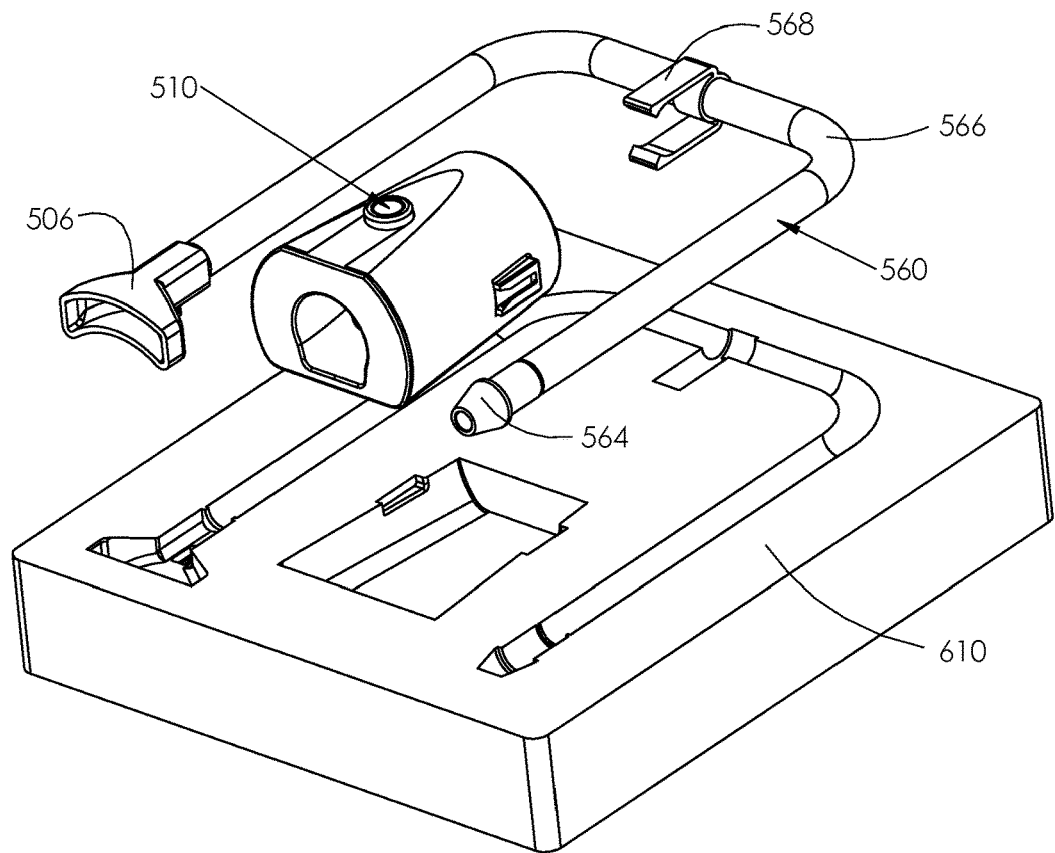
FIG. 94 is an exploded perspective view of a kit having a packaging enclosure configured to retain the lighting device and smoke evacuation assembly shown in FIG. 61.
Figure 95:
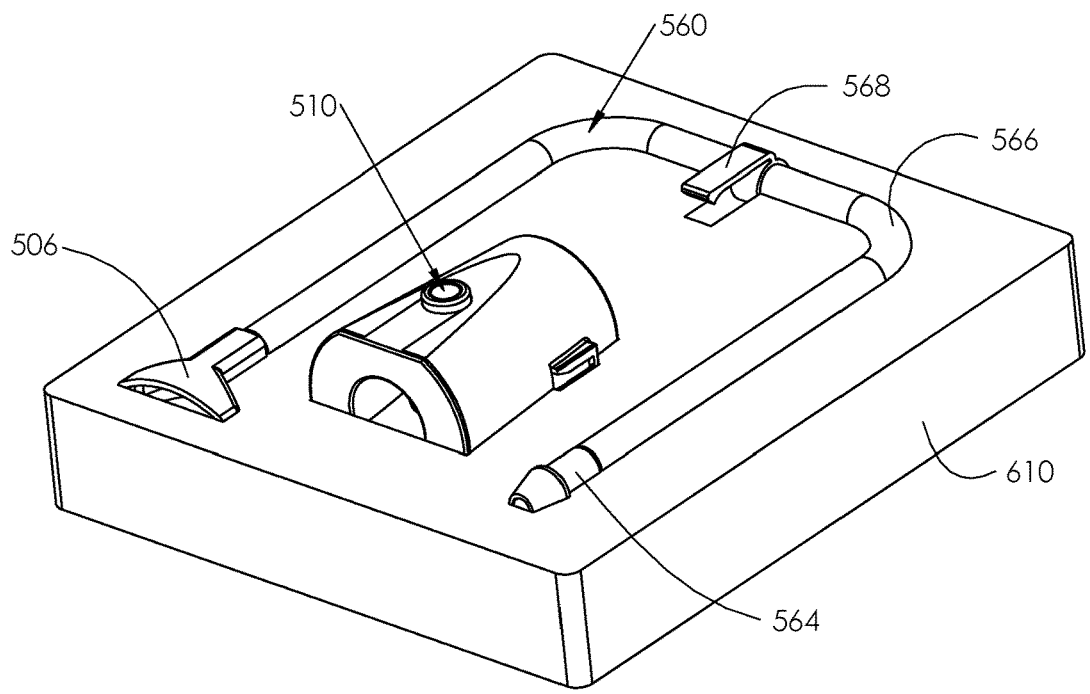
FIG. 95 is a perspective view of the kit shown in FIG. 94 with the lighting device and smoke evacuation assembly packaged within the enclosure.
Figure 96:
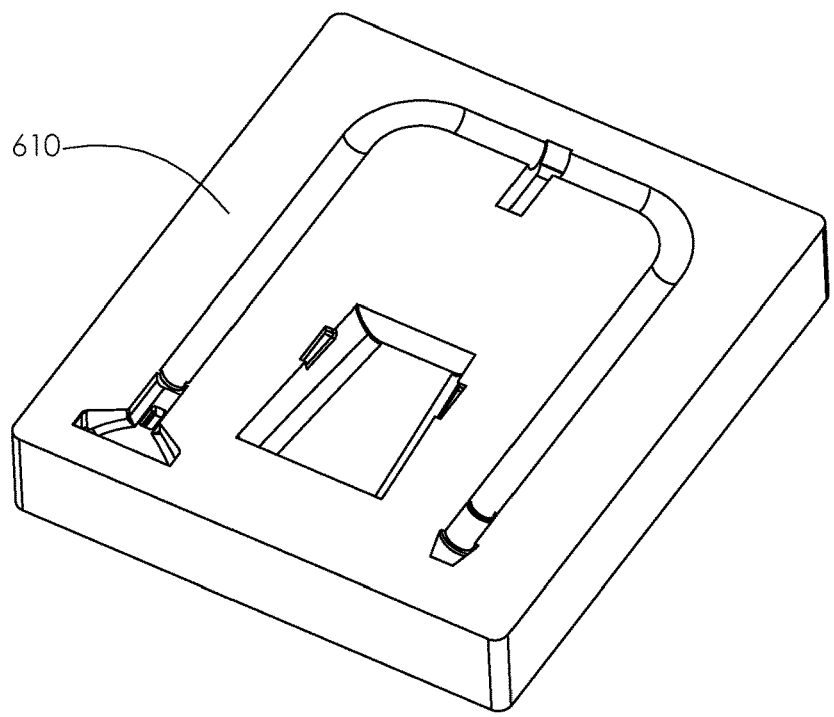
FIG. 96 is a top perspective view of the packaging enclosure shown in FIG. 94.
Figure 97:
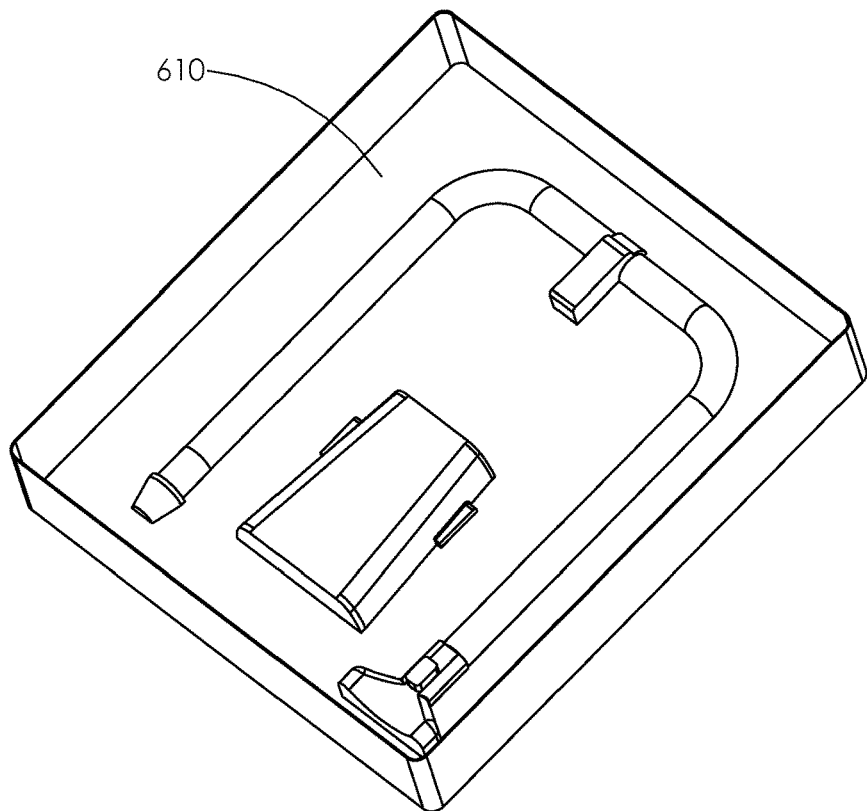
FIG. 97 is a bottom perspective view of the packaging enclosure shown in FIG. 94.

Referring to FIGS. 87 through 89, there is illustrated a cylindrical or tube-shaped smoke evacuation inlet nozzle 602 having a distal inlet portion 602 and a proximal outlet portion 606 which is dimensioned and configured for communication with a smoke evacuation tube 586. Those skilled in the art will readily appreciate that inlet nozzle 602 can be employed as an alternative nozzle feature of any of the smoke evacuation assemblies described and illustrated herein.

Referring to FIGS. 90 through 93, there is illustrated another smoke evacuation inlet nozzle 605 that includes a rear body portion 608 that is configured for communication with a smoke evacuation tube 586 and a multi-orifice front body portion 612 configured to distribute suction across a distance to better pull surgical smoke covering a wider area in the surgical field. Those skilled in the art will readily appreciate that a multi-orifice nozzle like nozzle 605, shown in FIG. 90 can be employed as an alternative nozzle feature of any of the smoke evacuation assemblies described and illustrated herein.

Figure 61:
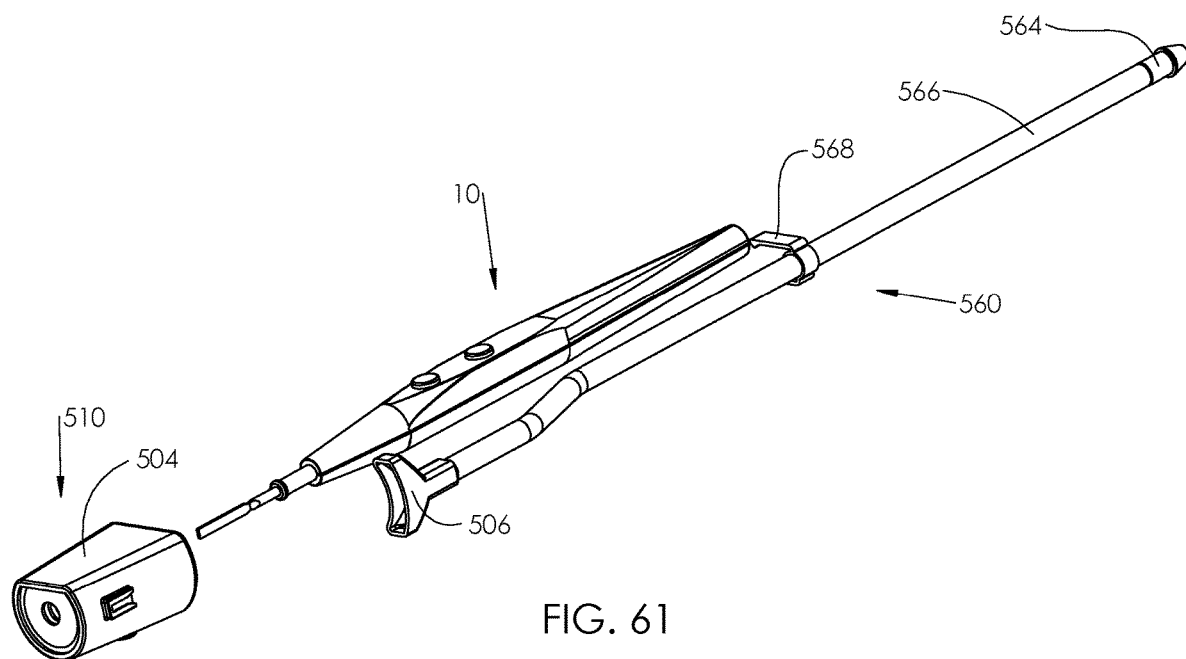
FIG. 61 is a perspective view similar to that of FIG. 46, wherein the smoke evacuation tube extending from the nozzle assembly includes a clip for engaging a proximal end portion of the surgical instrument.
Figure 62:
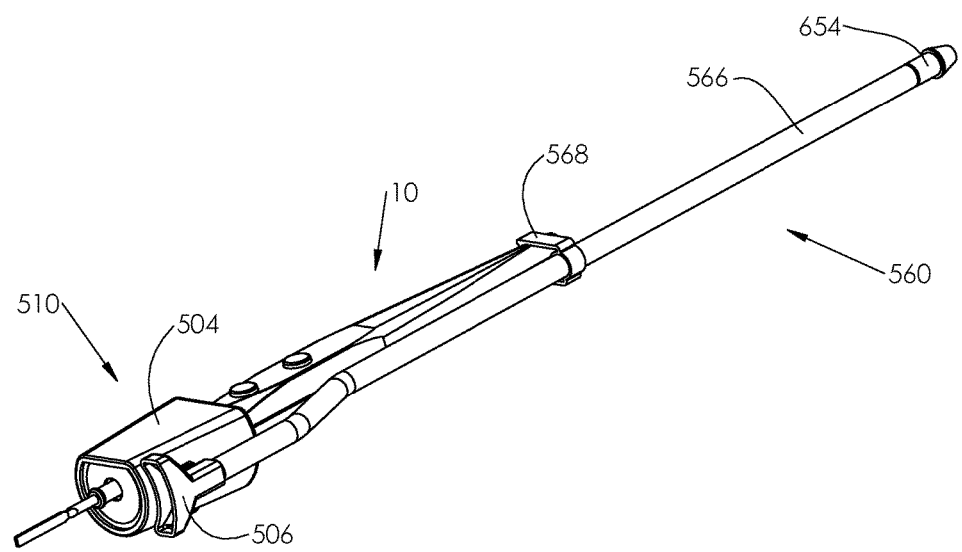
FIG. 62 is a perspective view as in FIG. 61, with the clip on the smoke evacuation tube engaged to the proximal end portion of the surgical instrument.
Figure 63:
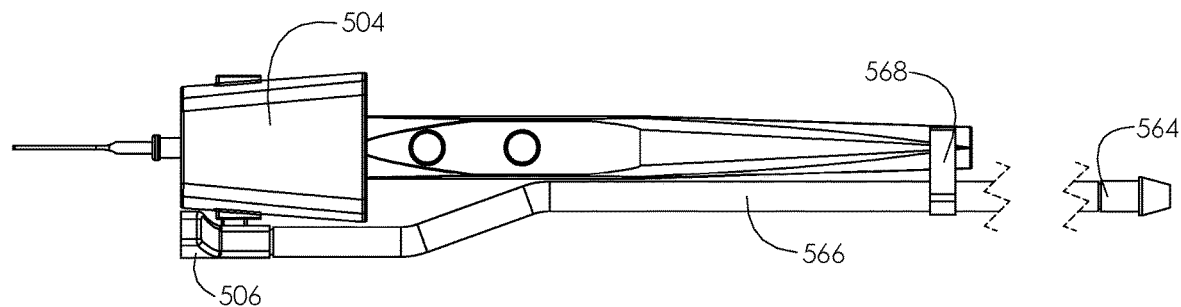
FIG. 63 is a top plan view of the assembly shown in FIG. 62.
Figure 64:
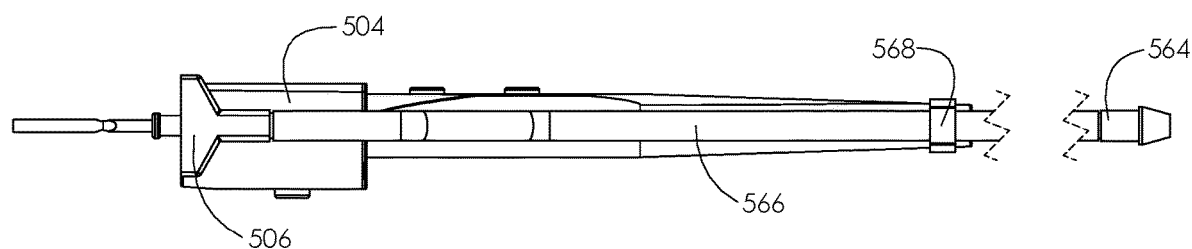
FIG. 64 is a right side elevational view of the assembly shown in FIG. 62.

Referring now to FIGS. 94 through 97, there is illustrated a kit for performing a surgical procedure with a handheld surgical instrument, that includes a packaging enclosure 610 configured to retain a battery powered lighting device 510 and detachable smoke evacuation assembly 560 shown in FIGS. 61 and 62. The smoke evacuation assembly 560 includes a nozzle inlet 506, an elongated tube 566 having a proximal connector 564 and a clip 568 for attachment to the proximal end of a hand held surgical instrument.

Figure 98:
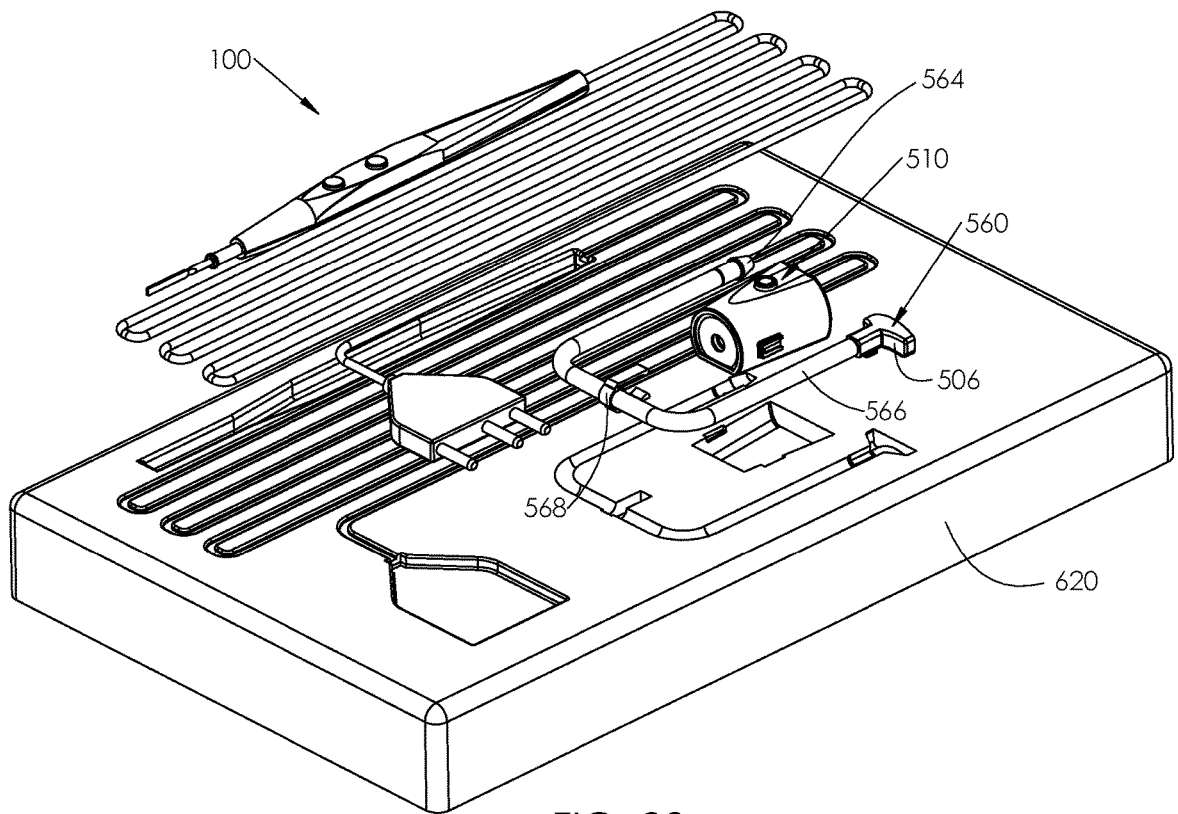
FIG. 98 is an exploded perspective view of a kit having a packaging enclosure configured to retain the lighting device, smoke evacuation assembly and surgical instrument shown in FIG. 61, wherein the surgical instrument has a connective wire (those skilled in the art will readily appreciate that the wire was excluded in previous drawings for ease of illustration)
Figure 99:
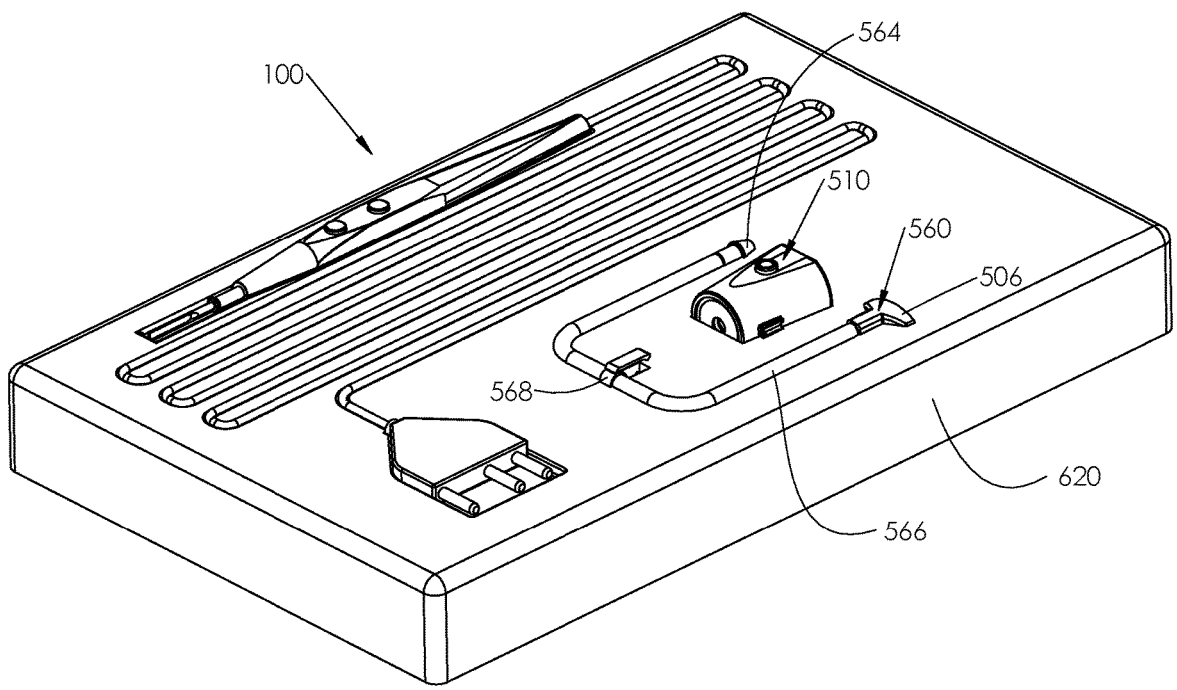
FIG. 99 is a perspective view of the kit shown in FIG. 98 with the lighting device, smoke evacuation assembly and surgical instrument packaged within the enclosure.
Figure 100:
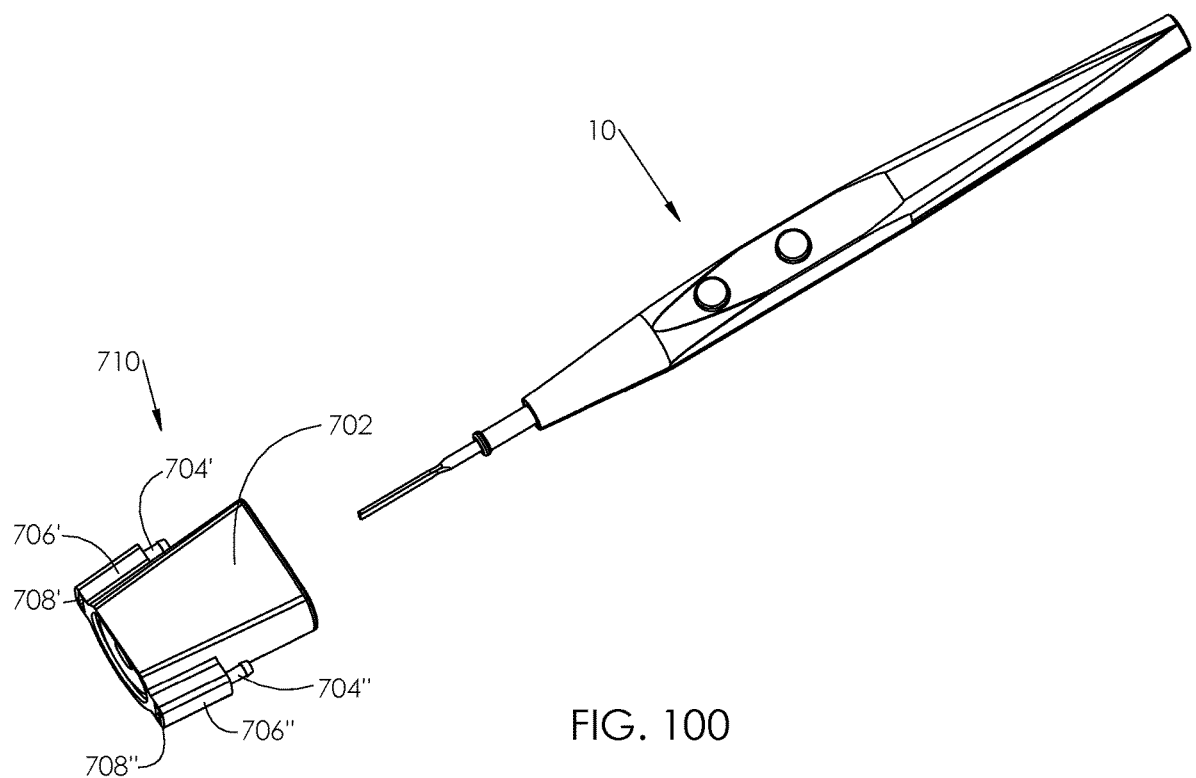
FIG. 100 is perspective view of another lighting device separated from a surgical instrument to which it may be attached, which includes multiple external smoke evacuation passages.
Figure 101:
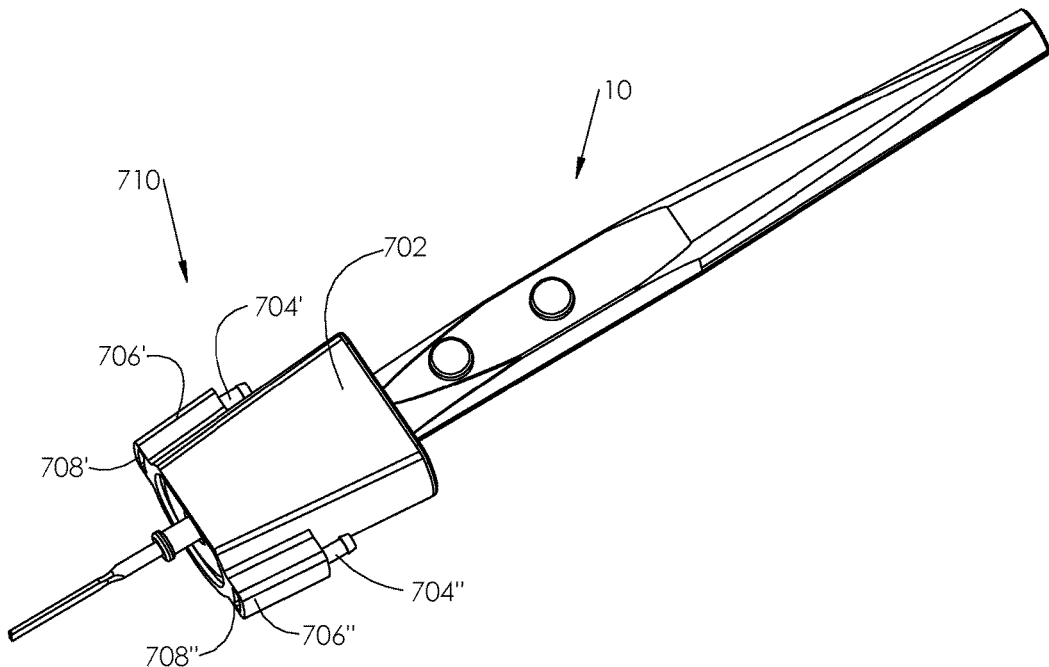
FIG. 101 is a perspective view of as in FIG. 100 with the lighting device attached to the distal end portion of the surgical instrument.

Referring now to FIGS. 98 through 99, there is illustrated another kit for performing a surgical procedure, which includes a packaging enclosure 620 configured to retain a battery powered lighting device 510, a smoke evacuation assembly 560 for attachment to the lighting device 510 and a handheld electrocautery instrument 100 (such as a BOVIE® pencil or the like) to which the lighting device 510 is attached for illuminating the surgical site without unduly obstructing the surgeons line of sight. With this kit, a surgeon can perform an electrocautery procedure and perform smoke evacuation while illuminating the surgical site.

Turning now to FIGS. 100 through 107, there is illustrated yet another embodiment of a lighting device with an integral smoke evacuation assembly designated generally by reference numeral 710, which is also designed for use with a handheld electrosurgical instrument 10. Lighting device 710 includes a generally conical housing 702 that includes integral right and left smoke evacuation passages 706' and 706". Each smoke evacuation passage has an inlet 708' and 708" adjacent or near the distal end of the housing 702 for drawing in smoke and an outlet barb 704' and 704" adjacent or near the proximal end of the housing 702 for communicating with a smoke evacuation tube 720.

Figure 102:
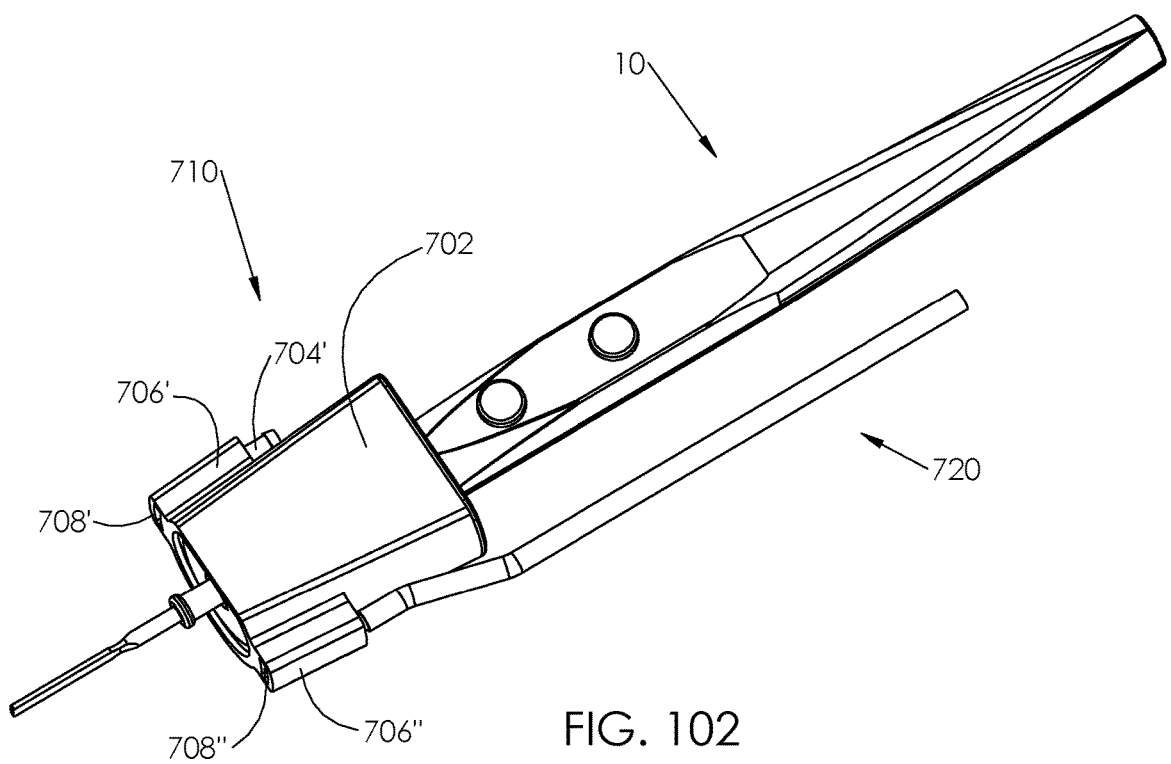
FIG. 102 is a perspective view of the assembly shown in FIG. 101, with a smoke evacuation tube connected to the smoke evacuation passage on the right side of the lighting device.
Figure 103:
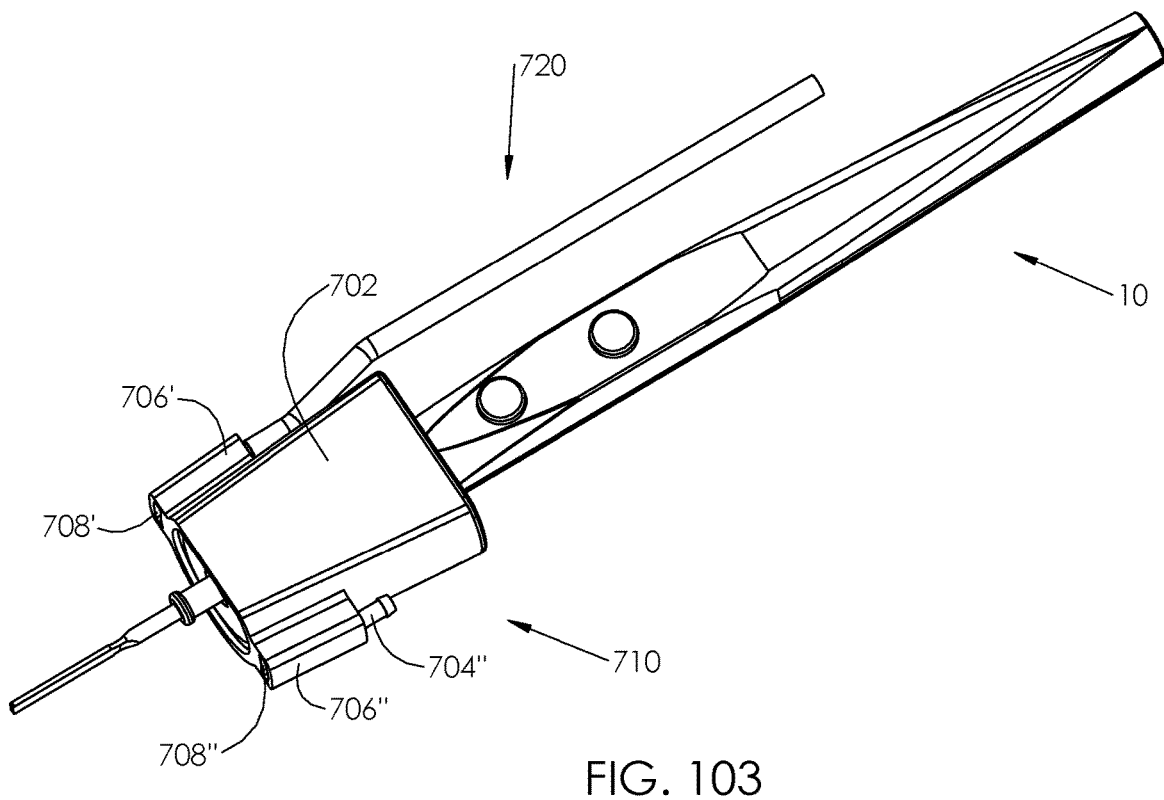
FIG. 103 is a perspective view of the assembly shown in FIG. 101, with a smoke evacuation tube connected to the smoke evacuation passage on the left side of the lighting device.
Figure 104:
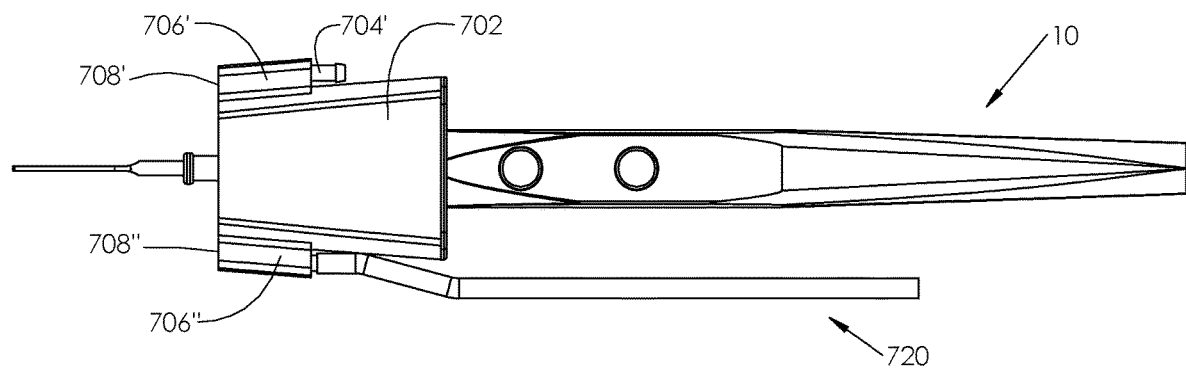
FIG. 104 is a top plan view of the assembly shown in FIG. 102.
Figure 105:
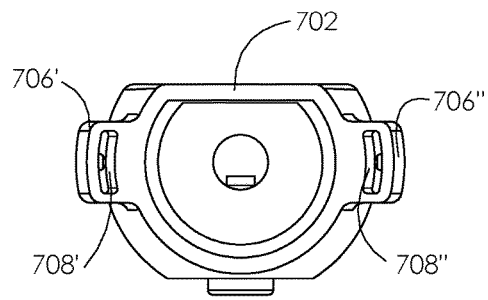
FIG. 105 is a front end view of the lighting device shown in FIG. 100.
Figure 106:
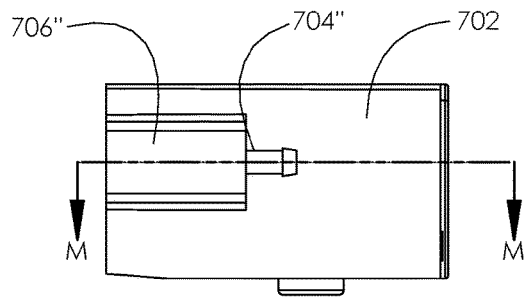
FIG. 106 is a side elevational view of the lighting device shown in FIG. 100.
Figure 107:
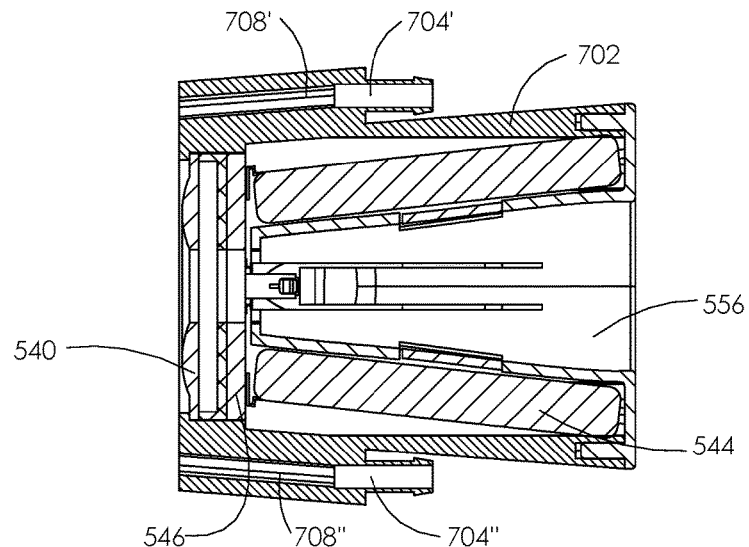
FIG. 107 is a cross-sectional view taken along line N-N of FIG. 106.
Figure 108:
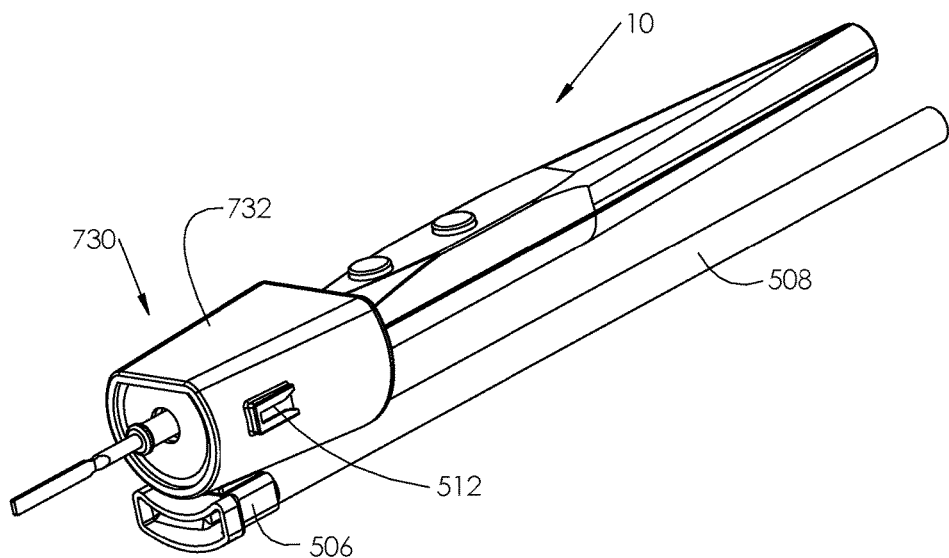
FIG. 108 is a perspective view of a lighting device attached to the distal end portion of a surgical instrument, wherein the lighting device has multiple distinct attachment locations for attaching a smoke evacuation passage thereto, and wherein the inlet nozzle of a smoke evacuation passage is attached to a bottom one of those attachment locations.
Figure 109:
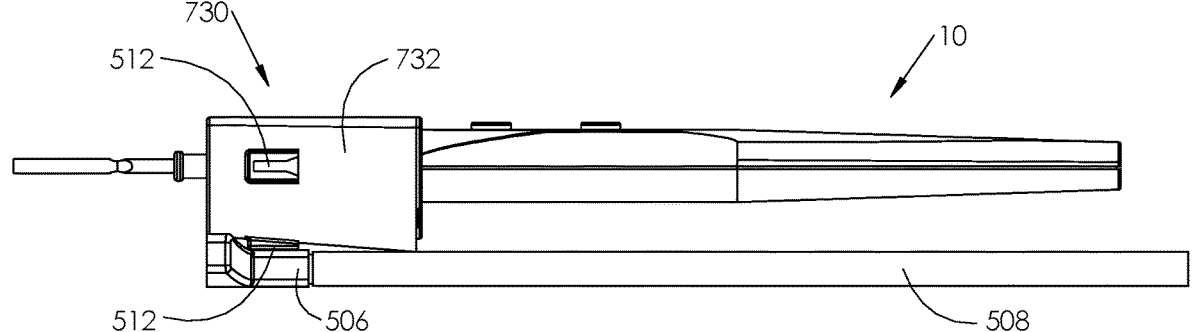
FIG. 109 is a side elevational view of the assembly shown in FIG. 108.

As best seen in FIG. 107, lighting device 710 has an interior cavity with a conical alignment sleeve 556 and a lighting assembly which includes a printed circuit board 546 having one or more embedded LED light sources and one or more battery cells 544. A lens 540 is positioned at the distal end of the housing 702. In use, performing a surgical procedure with lighting device 710 including the steps of attaching the lighting device 710 to the distal end portion of the surgical instrument 10, which activates the LED light sources, and then connecting the outlet 704 of one of the smoke evacuation passage 706' or 706" to a source of suction by way of smoke evacuation tube 720. If necessary, during the procedure, in order to prevent obstruction of the operative site by the smoke evacuation tube 720, the method further includes the steps of detaching the smoke evacuation tube 720 from one of the smoke evacuation passage 706' or 706" and reattaching the smoke evacuation tube 720 to the other smoke evacuation passage 706' or 706", as illustrated in FIGS. 102 and 103.

Figure 110:
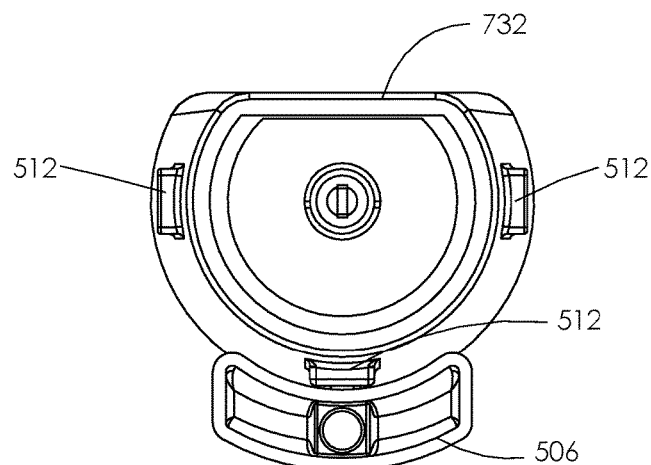
FIG. 110 is a front end view of the assembly shown in FIG. 108.

Referring now to FIGS. 108 through 113, there is illustrated a lighting device 730 for use with a handheld surgical instrument 10 that has three distinct attachment locations (it is envisioned that there could be more than three attachment locations) for engagement with the inlet nozzle 506 of a detachable smoke evacuation assembly having an elongated smoke evacuation tube 508 for communicating with a smoke evacuator or pump (not shown). More particularly, as best seen in FIG. 110, the generally conical housing 732 of lighting device 730 includes a first attachment flange 512 on the right side of the housing 732, a second attachment flange 512' on the left side of the housing 732 and a third attachment flange 512" on the bottom of the housing 732.

Figure 111:
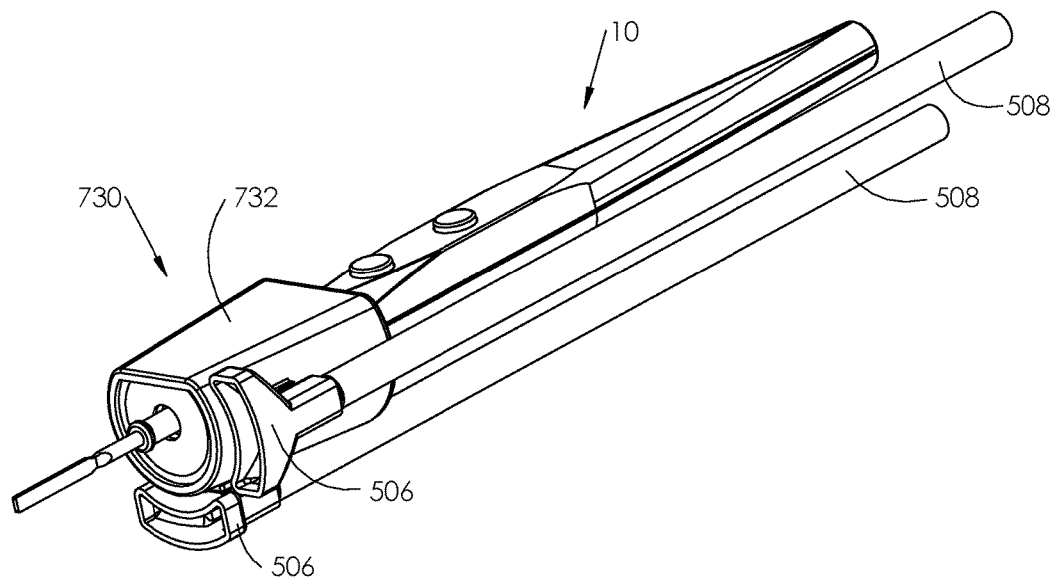
FIG. 111 is perspective view of the assembly shown in FIG. 108 with the inlet nozzles of two separated two smoke evacuation passages are attached to the lighting device at two different locations.
Figure 112:
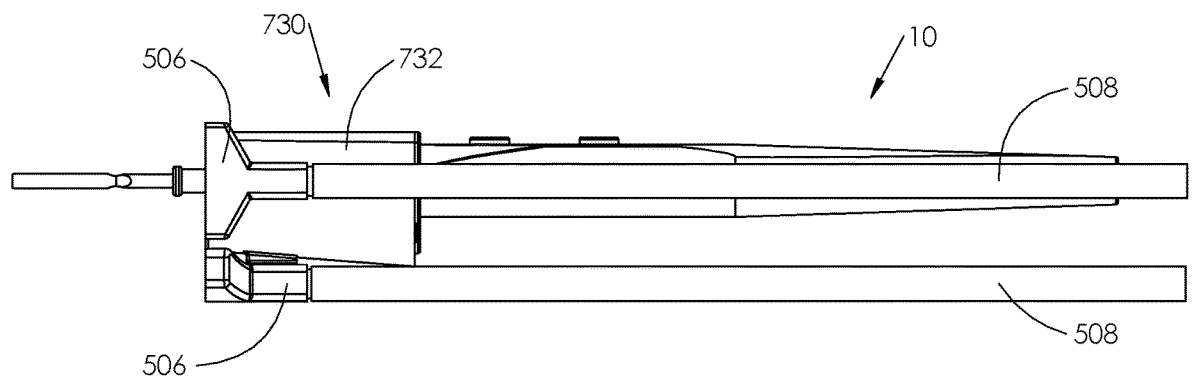
FIG. 112 is a side elevational view of the assembly shown in FIG. 111.
Figure 113:
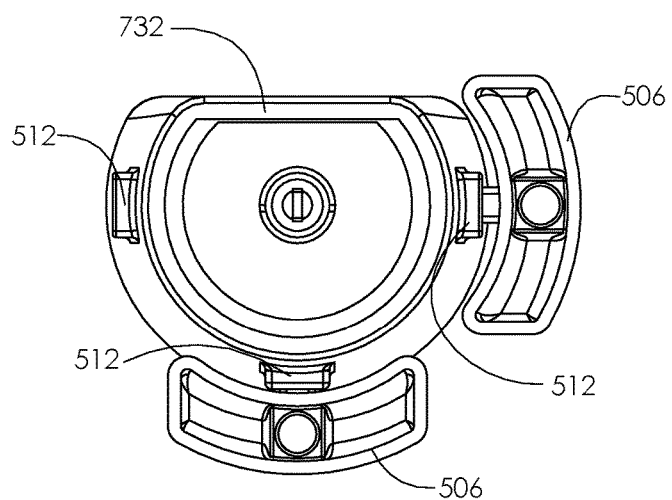
FIG. 113 is a front end view of the assembly shown in FIG. 111.

It is envisioned that the inlet nozzle 506 of a smoke evacuation assembly can be attached at either of the three or more locations. Alternatively, as illustrated in FIGS. 111 through 113, the inlet nozzles 506 of more than one smoke evacuation assembly can be attached to the housing 732 of the lighting device 730 to enhance the smoke evacuation effectiveness of the system.

While the subject disclosure has been shown and described with reference to preferred embodiments, those skilled in the art will readily appreciate that changes or modifications may be made thereto without departing from the spirit or scope of the subject disclosure.

What is claimed is:

1. A lighting device for attachment to a handheld electrosurgical instrument comprising: an elongated housing having opposed proximal and distal end portions and defining an interior chamber containing a battery powered lighting assembly for illuminating a surgical site, the housing having at least one smoke evacuation passage associated therewith that extends from an inlet located near the distal end portion of the housing to an outlet located near the proximal end portion of the housing for removing smoke generated at the surgical site, wherein the smoke evacuation passage is located within the housing of the lighting device, separated from the interior chamber by an interior wall of the housing, wherein the housing includes a clamping mechanism for selectively attaching the lighting device to the surgical instrument, wherein the clamping mechanism for selectively attaching the lighting device include a generally U-shaped clamp body having a pair of opposed parallel clamping arms, and wherein an adjustable holding screw is associated with one clamping arm and an interior surface of the other clamping arm has a compliant material plate thereon.

2. A lighting device as recited in claim 1, wherein the smoke evacuation passage has one of a rectangular cross-sectional configuration, a square cross-sectional configuration, an oval cross-sectional configuration or a circular cross-sectional configuration.

3. A lighting device as recited in claim 1, wherein a connective fitting is associated with the outlet of the smoke evacuation passage for connecting the smoke evacuation passage with a smoke evacuation tube that communicates with a source of suction.

4. A lighting device as recited in claim 3, wherein an actuation button is associated with the housing for actuating the switching mechanism.

5. A lighting device as recited in claim 1, wherein the battery powered lighting assembly includes a printed circuit board that includes at least one LED lighting component, at least one battery cell, and a switching mechanism.

6. A lighting device for attachment to a handheld electrosurgical instrument comprising: an elongated housing having opposed proximal and distal end portions and defining an interior chamber containing a battery powered lighting assembly for illuminating a surgical site, the housing having at least one smoke evacuation passage associated therewith that extends from an inlet located near the distal end portion of the housing to an outlet located near the proximal end portion of the housing for removing smoke generated at the surgical site, wherein the smoke evacuation passage is located within the housing of the lighting device, separated from the interior chamber by an interior wall of the housing, wherein the housing includes a clamping mechanism for selectively attaching the lighting device to the surgical instrument, wherein the clamping mechanism is pivotably connected to the housing about a pivot axis that extends perpendicular to a longitudinal axis of the elongated housing.

* * * * *